(12) United States Patent
Huang

(10) Patent No.: US 11,819,194 B2
(45) Date of Patent: Nov. 21, 2023

(54) ENDOSCOPE MODULE

(71) Applicant: Shi-Hwa Huang, New Taipei (TW)

(72) Inventor: Shi-Hwa Huang, New Taipei (TW)

( * ) Notice: Subject to any disclaimer, the term of this patent is extended or adjusted under 35 U.S.C. 154(b) by 47 days.

(21) Appl. No.: 17/485,483

(22) Filed: Sep. 26, 2021

(65) Prior Publication Data

US 2022/0257103 A1 Aug. 18, 2022

(30) Foreign Application Priority Data

Feb. 17, 2021 (TW) .................. 110105406

(51) Int. Cl.
| | |
|---|---|
| A61B 1/05 | (2006.01) |
| G02B 5/04 | (2006.01) |
| A61B 1/06 | (2006.01) |
| A61B 1/045 | (2006.01) |

(52) U.S. Cl.
CPC .............. *A61B 1/051* (2013.01); *A61B 1/045* (2013.01); *A61B 1/0607* (2013.01); *A61B 1/0638* (2013.01); *G02B 5/04* (2013.01)

(58) Field of Classification Search
CPC . A61B 1/00096; A61B 1/00105; A61B 1/045; A61B 1/05; A61B 1/0607; A61B 1/0615; A61B 1/00163; A61B 1/00174; G02B 5/04

See application file for complete search history.

(56) References Cited

U.S. PATENT DOCUMENTS

| | | | |
|---|---|---|---|
| 6,333,826 B1 * | 12/2001 | Charles | |
| 2009/0118580 A1 * | 5/2009 | Sun et al. | |
| 2011/0261569 A1 * | 10/2011 | Kayanuma | |
| 2013/0308033 A1 * | 11/2013 | Kuo | |
| 2017/0215714 A1 * | 8/2017 | Shinji et al. | |
| 2020/0110257 A1 | 4/2020 | Motohara et al. | |

FOREIGN PATENT DOCUMENTS

| | | |
|---|---|---|
| CN | 211905838 | 11/2020 |
| CN | 212540868 | 2/2021 |
| TW | 201348730 | 12/2013 |

OTHER PUBLICATIONS

Shirakawa et al. "An 8-Tap CMOS Lock-In Pixel Image Sensor for Short-Pulse Time-of-Flight Measurements". Feb. 2020. Sensors, MDPI, pp. 1-16. (Year: 2020).*
Shi-Hwa Huang, "Endoscope Module and Image Sensor", Unpublished Taiwan application No. 109118192, Filed on May 29, 2020, with English abstract thereof, pp. 1-35.

* cited by examiner

*Primary Examiner* — Aaron B Fairchild
*Assistant Examiner* — Julianna J Nicolaus
(74) *Attorney, Agent, or Firm* — JCIPRNET

(57) ABSTRACT

An endoscope module including an annular prism, an annular lens, an annular stop, and an annular image sensor is provided. The annular prism has an annular reflective inclined surface, a light incident surface, and a light emitting surface. The light incident surface faces a side surface and the light emitting surface faces away from a front surface. The annular stop is disposed on a side of the light incident surface of the annular prism and surrounds the annular prism. The annular lens is disposed between the annular prism and the annular image sensor. A lateral light from the side surface is reflected to the annular lens by the annular reflective inclined surface after passing through the annular stop and then entering the annular prism, and is then condensed to the annular image sensor by the annular lens.

15 Claims, 36 Drawing Sheets

ENDOSCOPE MODULE

CROSS-REFERENCE TO RELATED APPLICATION

This application claims the priority benefit of Taiwanese application no. 110105406, filed on Feb. 17, 2021. The entirety of the above-mentioned patent application is hereby incorporated by reference herein and made a part of this specification.

BACKGROUND

Technical Field

The disclosure relates to an optical module, and particularly to an endoscope module.

Description of Related Art

An endoscope plays an important role in examination inside a body and in minimally invasive procedures, in which it reaches deep into a human body to acquire some image information directly obtained from inside the human body, so as to achieve more accurate diagnosis and better surgical results.

However, for general endoscopes, only images within an effective viewing angle range in front of a lens can be obtained, preventing physicians from obtaining a full picture of the examined site. Although the lens of the endoscope may be rotated by a rotating mechanism to obtain the images of the examined site from different angles, this design increases the volume of the endoscope, and may thus indirectly burden the patient. In addition, the rotation of lens also involves image splicing, which may also indirectly result in misjudgment on the position of the affected part.

SUMMARY

The disclosure provides an endoscope module, in which a full picture of an object can be quickly sensed.

In an embodiment of the disclosure, an endoscope module includes an annular prism, an annular lens, an annular stop, and an annular image sensor. The annular prism has an annular reflective inclined surface, a light incident surface, and a light emitting surface. The light incident surface faces a side surface and the light emitting surface faces away from a front surface. The annular stop is disposed on a side of the light incident surface of the annular prism and surrounds the annular prism. The annular lens is disposed between the annular prism and the annular image sensor. A lateral light from the side surface is reflected to the annular lens by the annular reflective inclined surface after passing through the annular stop and then entering the annular prism, and is then condensed to the annular image sensor by the annular lens.

In an embodiment of the disclosure, an endoscope module includes a first sub-endoscope module and at least one second sub-endoscope module. The first sub-endoscope module includes a first annular prism, a first annular lens, a first annular stop, and a first annular image sensor. The first annular prism has a first annular reflective inclined surface, a first light incident surface, and a first light emitting surface. The first light incident surface faces a side surface and the first light emitting surface faces away from a front surface. The first annular stop is disposed on a side of the first light incident surface of the first annular prism and surrounds the first annular prism. The first annular lens is disposed between the first annular prism and the first annular image sensor. A first lateral light from the side surface is reflected to the first annular lens by the first annular reflective inclined surface after passing through the first annular stop and then entering the first annular prism, and is then condensed to the first annular image sensor by the first annular lens. The second sub-endoscope module is disposed on a side of the first sub-endoscope module. Each second sub-endoscope module includes a second annular prism, a second annular lens, a second annular stop, and a second annular image sensor. The second annular prism has a second annular reflective inclined surface, a second light incident surface, and a second light emitting surface. The second light incident surface faces the side surface and the second light emitting surface faces away from the front surface. The second annular stop is disposed on a side of the second light incident surface of the second annular prism and surrounds the second annular prism. The second annular lens is disposed between the second annular prism and the second annular image sensor. A second lateral light from the side surface is reflected to the second annular lens by the second annular reflective inclined surface after passing through the second annular stop and then entering the second annular prism, and is then condensed to the second annular image sensor by the second annular lens.

Based on the foregoing, in the endoscope module of an embodiment of the disclosure, since the annular prism and the annular lens are adopted to transmit the lateral light from the side surface to the annular image sensor, the endoscope module may sense the image of the object to be detected on the side surface.

In addition, in another embodiment of the disclosure, since the endoscope module includes the first sub-endoscope module and the at least one second sub-endoscope module, the endoscope module can complete the scanning of the object to be detected within a shorter time, effectively reducing the detection time.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1A:
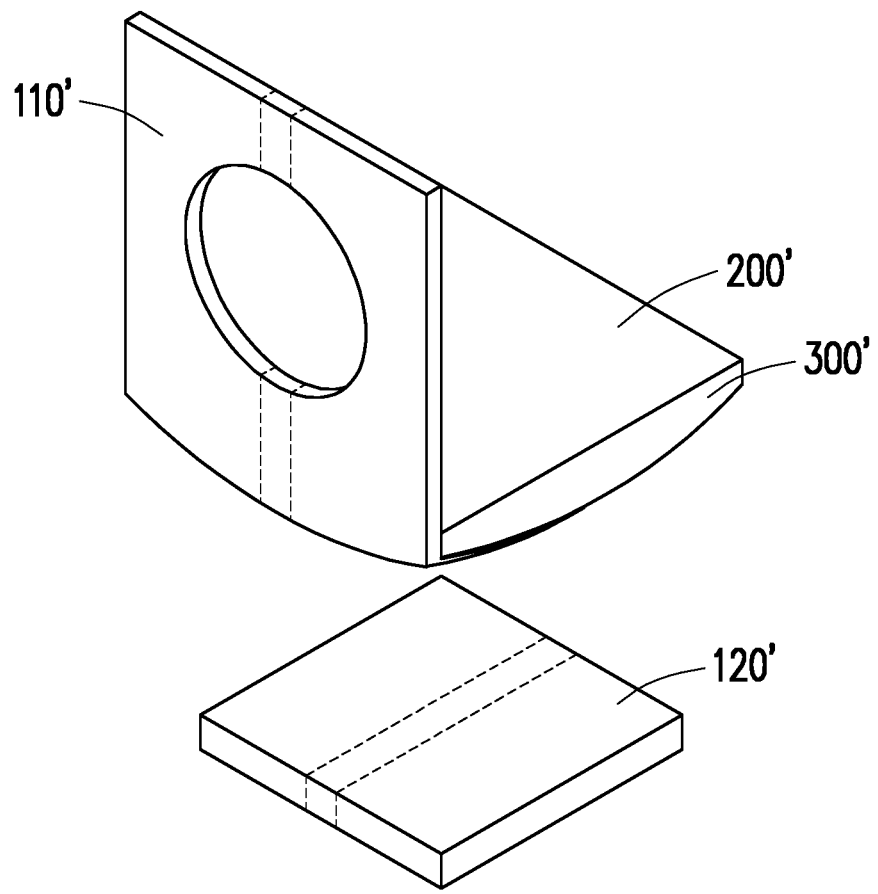
FIG. 1A is a conceptual diagram of an endoscope module according to an embodiment of the disclosure.
Figure 1B:
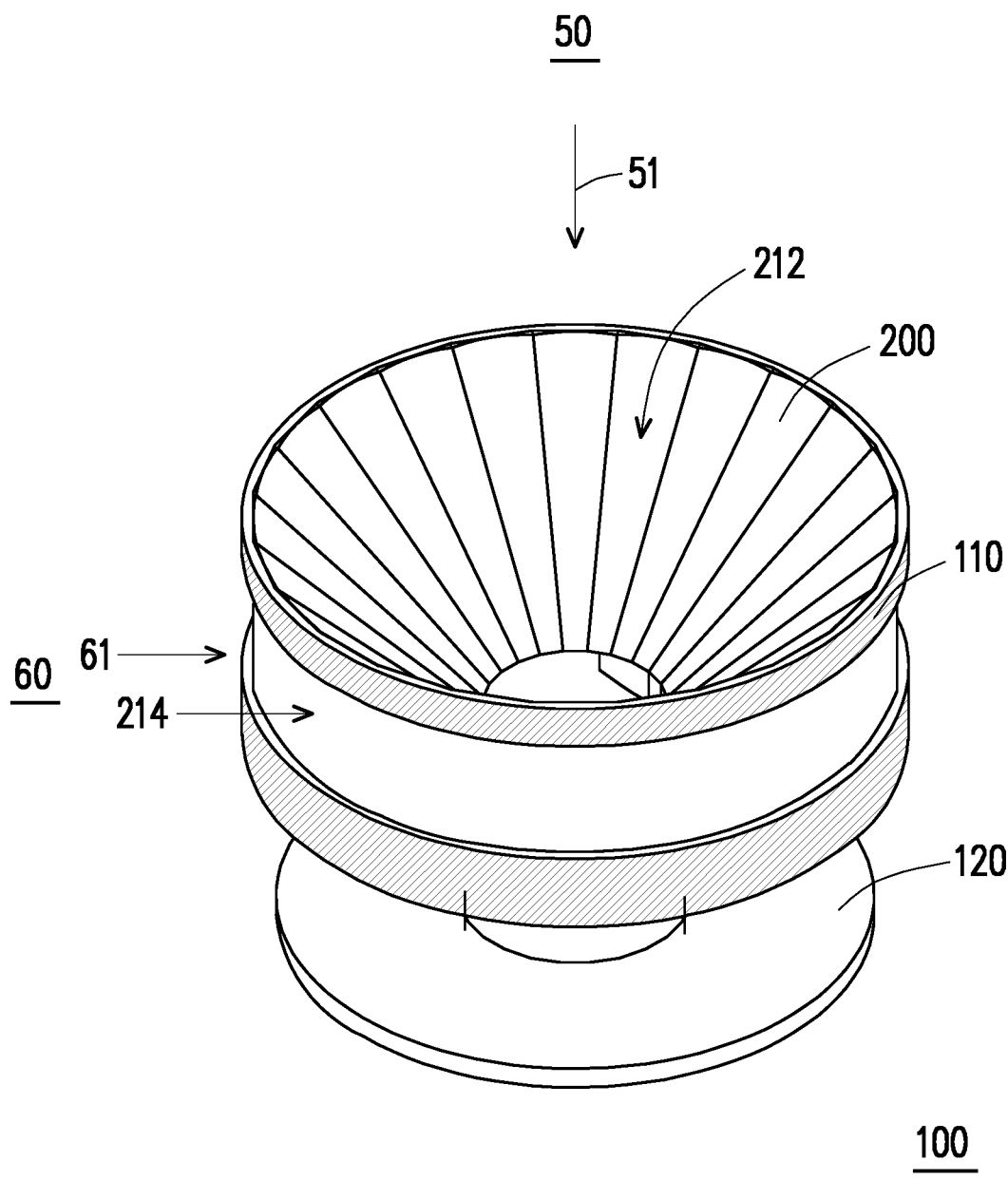
FIG. 1B is a schematic perspective view of an endoscope module according to a first embodiment of the disclosure.
Figure 1C:
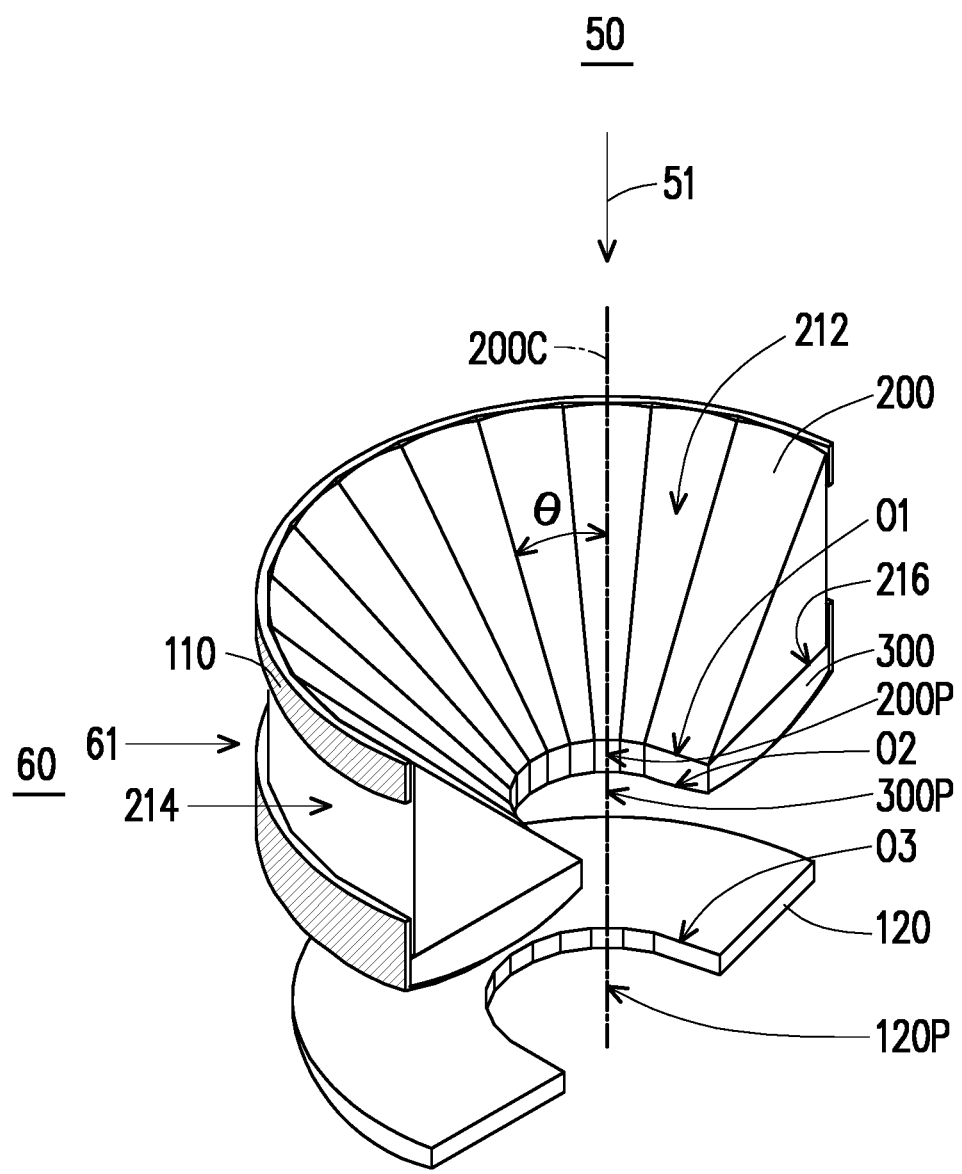
FIG. 1C is a schematic perspective view of the endoscope module of FIG. 1B cut along a central axis 200C.
Figure 1D:
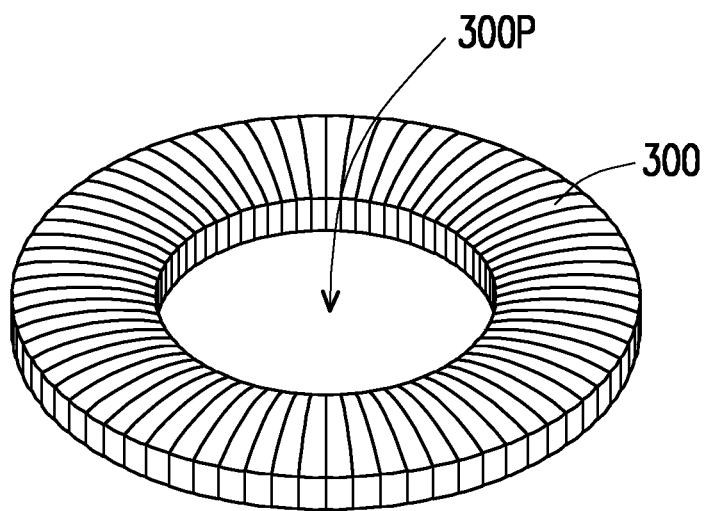
FIG. 1D is a schematic perspective view of the annular lens of FIG. 1A.

FIG. 1A is a conceptual diagram of an endoscope module according to an embodiment of the disclosure. FIG. 1B is a schematic perspective view of an endoscope module according to a first embodiment of the disclosure. FIG. 1C is a schematic perspective view of the endoscope module of FIG. 1B cut along a central axis 200C. FIG. 1D is a schematic perspective view of the annular lens of FIG. 1A. With reference to FIG. 1A to FIG. 1D together, in FIG. 1A, the endoscope module includes a stop 110', a lens 200', a lens 300', and an image sensor 120'. A middle part of the endoscope module is obtained by slicing along the broken line of FIG. 1A, and then an endoscope module 100 of FIG. 1B is formed by combining a plurality of the middle parts.

To be specific, in an embodiment of the disclosure, the endoscope module 100 includes an annular prism 200, an annular lens 300, an annular stop 110, and an annular image sensor 120. The annular prism 200 has an annular reflective inclined surface 212, a light incident surface 214, and a light emitting surface 216. The light incident surface 214 faces a side surface 60 and the light emitting surface 216 faces away from a front surface 50. The annular reflective inclined surface 212 is adjacent to the light incident surface 214 and the light emitting surface 216.

In this embodiment, the annular stop 110 is disposed on a side of the light incident surface 214 of the annular prism 200 and surrounds the annular prism 200. In a preferred embodiment, the annular stop 110 may be directly disposed on the light incident surface 214. The annular stop 110 may be a black metal layer or a black optical thin film, but the disclosure is not limited thereto.

In this embodiment, the annular lens 300 is disposed between the annular prism 200 and the annular image sensor 120. In a preferred embodiment, the annular lens 300 and the annular prism 200 are integrally formed, further reducing the volume of the endoscope module 100 in the embodiment of the disclosure.

Figure 6A:
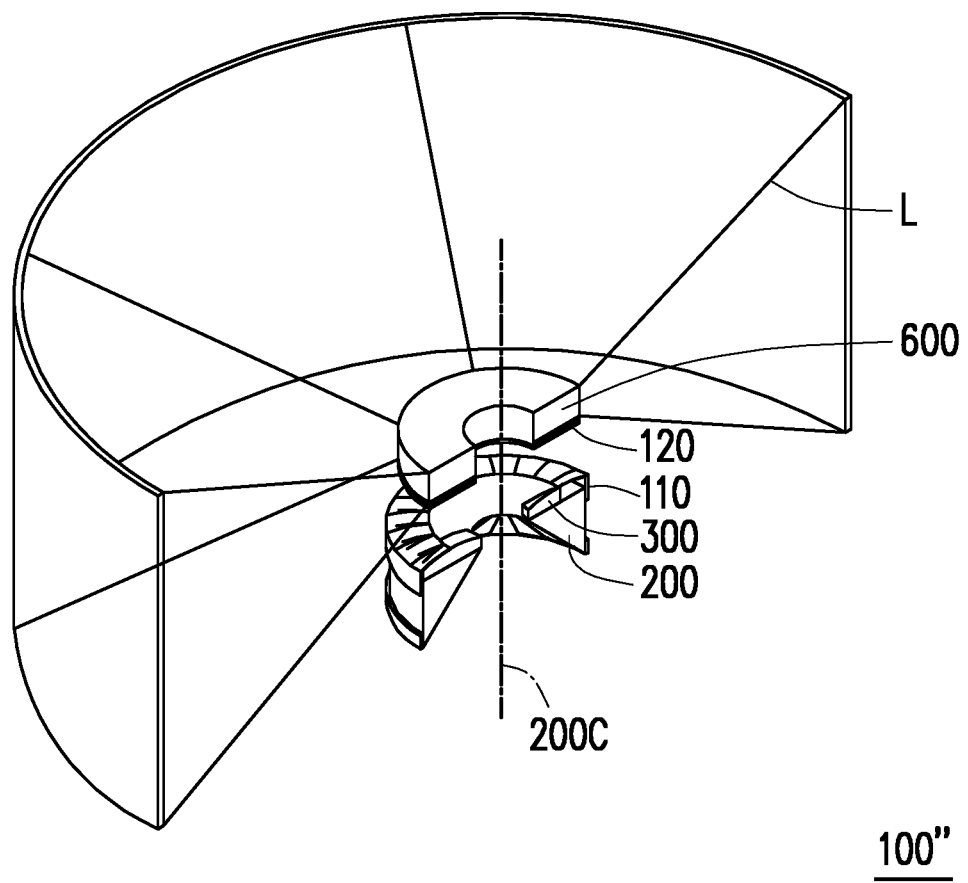
FIG. 6A is a perspective schematic view of an endoscope module according to a third embodiment of the disclosure cut along the central axis 200C.

In this embodiment, the endoscope module 100 may be provided with a light source (e.g., an annular light source 600 of FIG. 6A). An illumination light emitted by the light source irradiates an inner surface of an object to be detected and is reflected by the inner surface to generate a frontal light 51 facing the front surface 50 and a lateral light 61 facing the side surface 60 of the endoscope module 100. The front surface 50 is the side facing the annular reflective inclined surface 212 of the annular prism 200, and the side surface 60 is the side facing the light incident surface 214. Moreover, the lateral light 61 from the side surface 60 is (totally) reflected to the light emitting surface 216 by the annular reflective inclined surface 212 after passing through the annular stop 110 and then entering the annular prism 200 through the light incident surface 214. The lateral light 61 passes through the light emitting surface 216 and is transmitted to the annular lens 300, and is then condensed to the annular image sensor 120 by the annular lens 300.

In addition, in this embodiment, a cross section of the annular prism 200 along the central axis 200C is presented as a right triangle. In a preferred embodiment, an inclination angle θ of the annular reflective inclined surface 212 of the annular prism 200 relative to the central axis 200C of the annular prism 200 falls within a range of 45±3 degrees. Moreover, a cross section of the annular prism 200 along the central axis 200C is presented as an isosceles right triangle, such that the lateral light 61 incident from each direction can be imaged on the annular image sensor 120 with an orthographic projection. Therefore, the endoscope module 100 in the embodiment of the disclosure has better imaging quality.

Figure 2A:
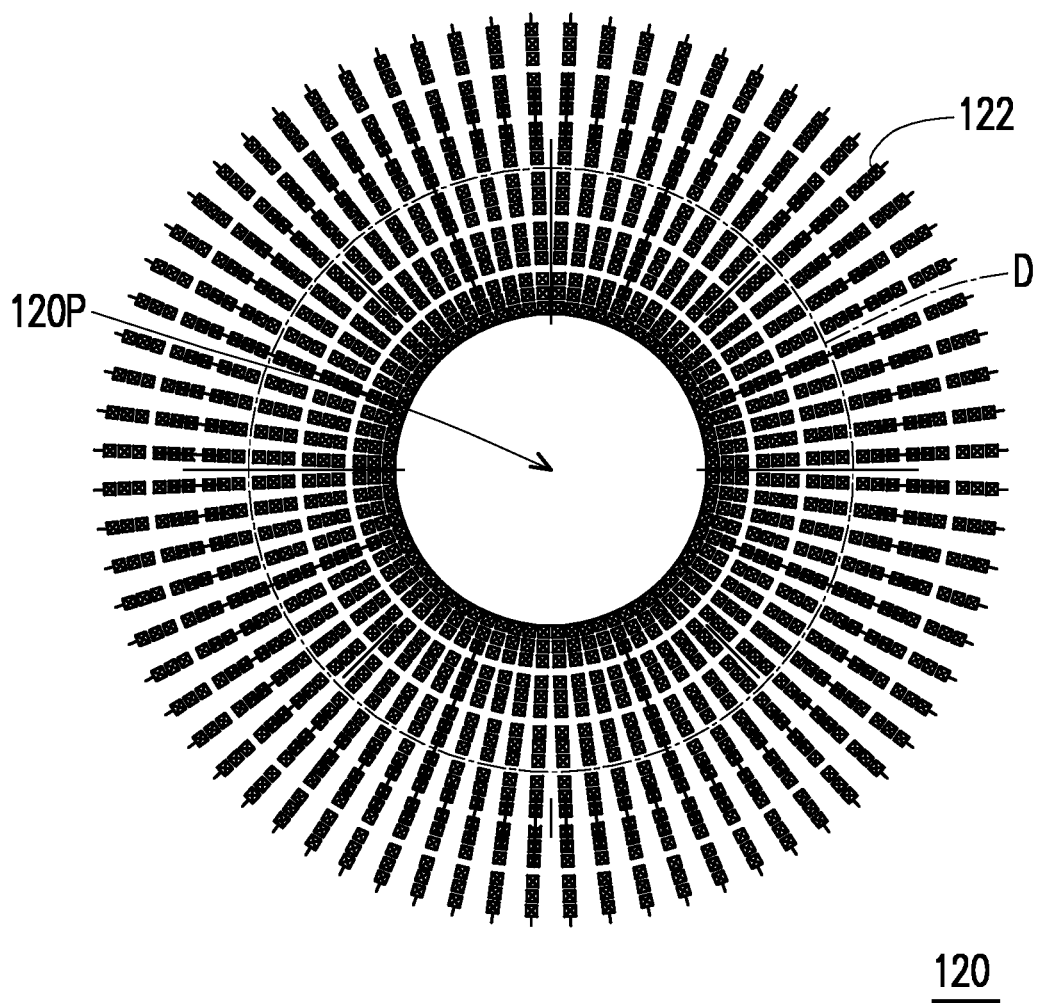
FIG. 2A is a schematic top view of an annular image sensor of an endoscope module according to an embodiment of the disclosure.
Figure 2B:
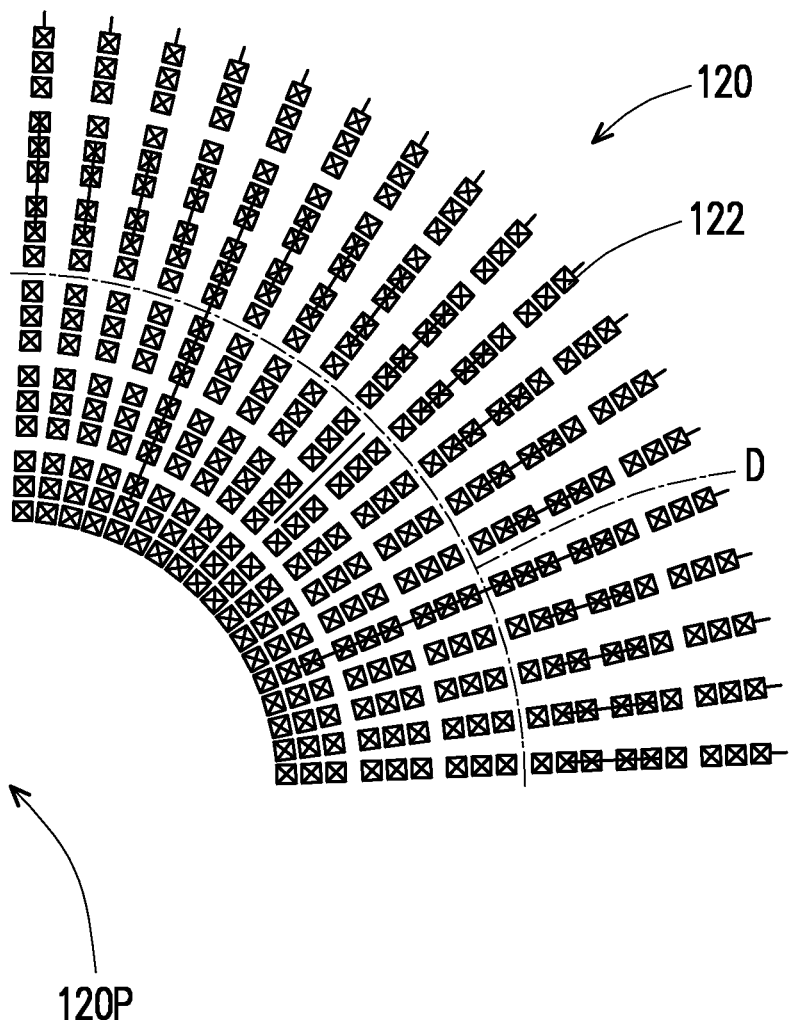
FIG. 2B is a partially enlarged view of FIG. 2A.
Figure 2C:
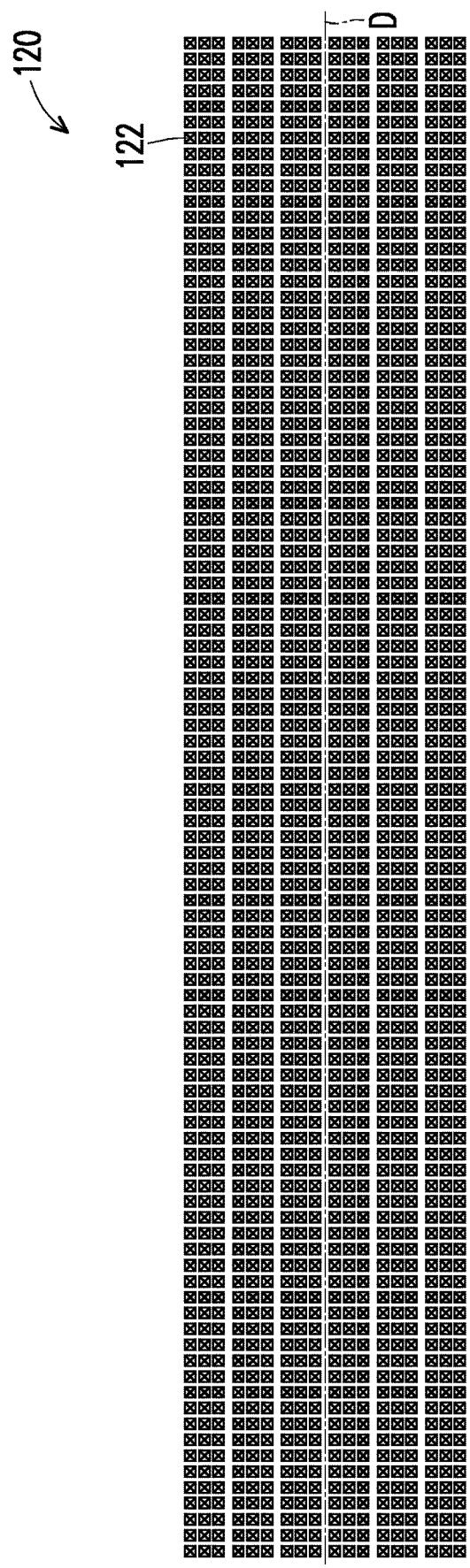
FIG. 2C is a schematic diagram of FIG. 2A after being unfolded along a central segmentation line D.

FIG. 2A is a schematic top view of an annular image sensor of an endoscope module according to an embodiment of the disclosure. FIG. 2B is a partially enlarged view of FIG. 2A. FIG. 2C is a schematic diagram of FIG. 2A after being unfolded along a central segmentation line D. With reference to FIG. 2A to FIG. 2C, in this embodiment, the annular image sensor 120 may be a light sensor of a complementary metal oxide semiconductor (CMOS) or a charge coupled device (CCD). The annular image sensor 120 has a plurality of first pixels 122, and the first pixels 122 are arranged radially and surround a center 120P of the annular image sensor 120. In addition, the pixel sizes of the first pixels 122 are the same as each other. Furthermore, the number of first pixels 122 within a range from the center 120P to the central segmentation line D of the annular image sensor 120 is the same as the number of first pixels 122 within a range beyond the central segmentation line D in a direction away from the center 120P. The central segmentation line D is a circular line centered at the center 120P.

In addition, for convenience of illustration, only some of the first pixels 122 are shown in FIG. 2A to FIG. 2C. In an embodiment, for example the embodiment of FIG. 2C, the first pixels 122 of the annular image sensor 120 are arranged into a 100×1024 matrix, and the size of each first pixel 122 is about 2×2 $\mu m^2$, but the disclosure is not limited thereto. The number of first pixels 122 may be determined depending on design requirements. Moreover, the annular image sensor 120 has a diameter of about 2.6 mm and a detectable wavelength range within a range of 435 nm to 940 nm, but the disclosure is not limited thereto.

With continued reference to FIG. 1B and FIG. 1C, in an embodiment, the diameter of the annular prism 200 of the endoscope module 100 is about 2.6 mm, the height (i.e., the maximum thickness of the endoscope module 100 along the central axis 200C) is about 3.6 mm, and the field angle of the endoscope module 100 on the side surface 60 is about 40 degrees (i.e., within a range of ±20 degrees).

Figure 3A:
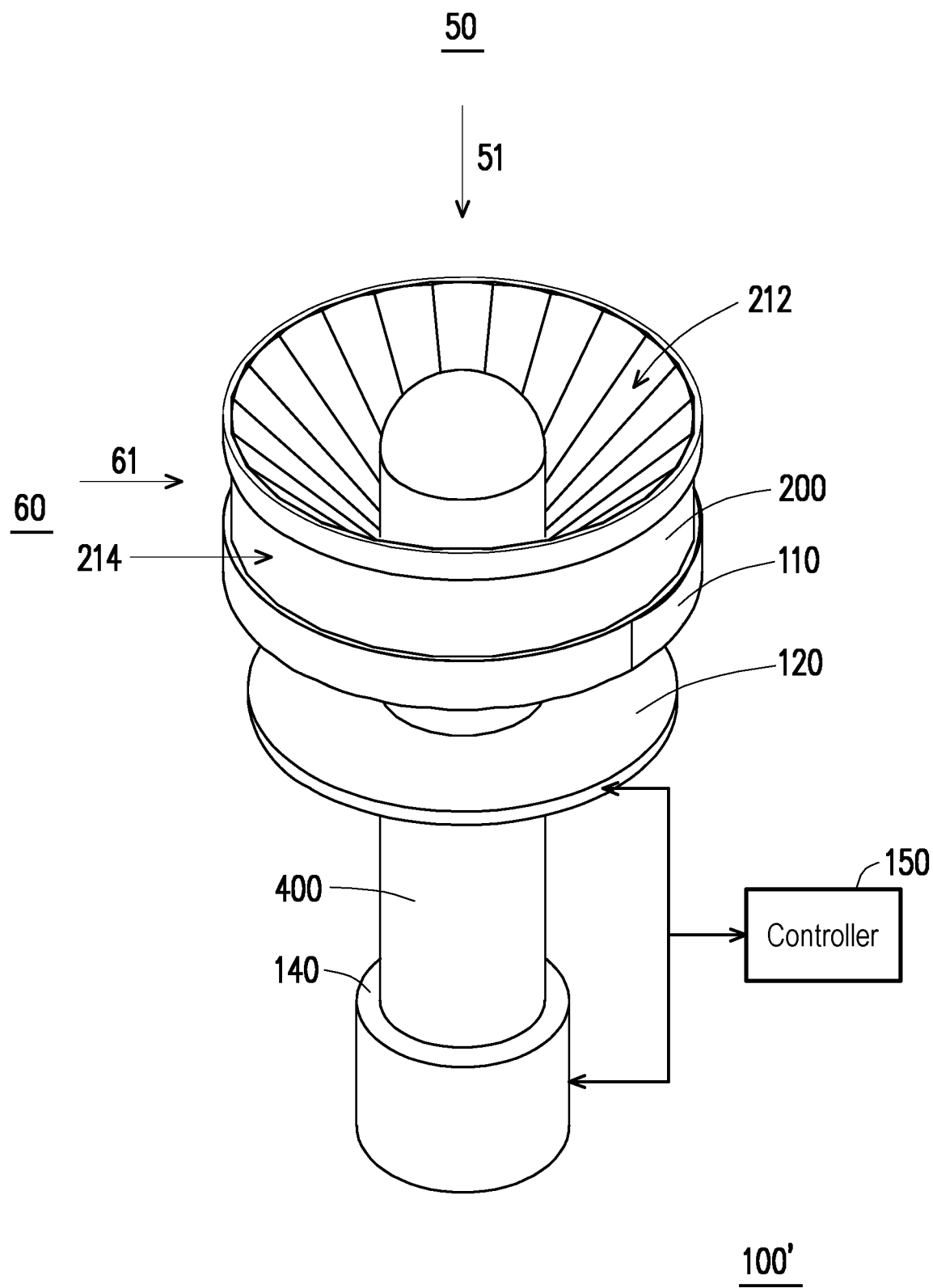
FIG. 3A is a schematic perspective view of an endoscope module provided with a fixing rod according to a second embodiment of the disclosure.
Figure 3B:
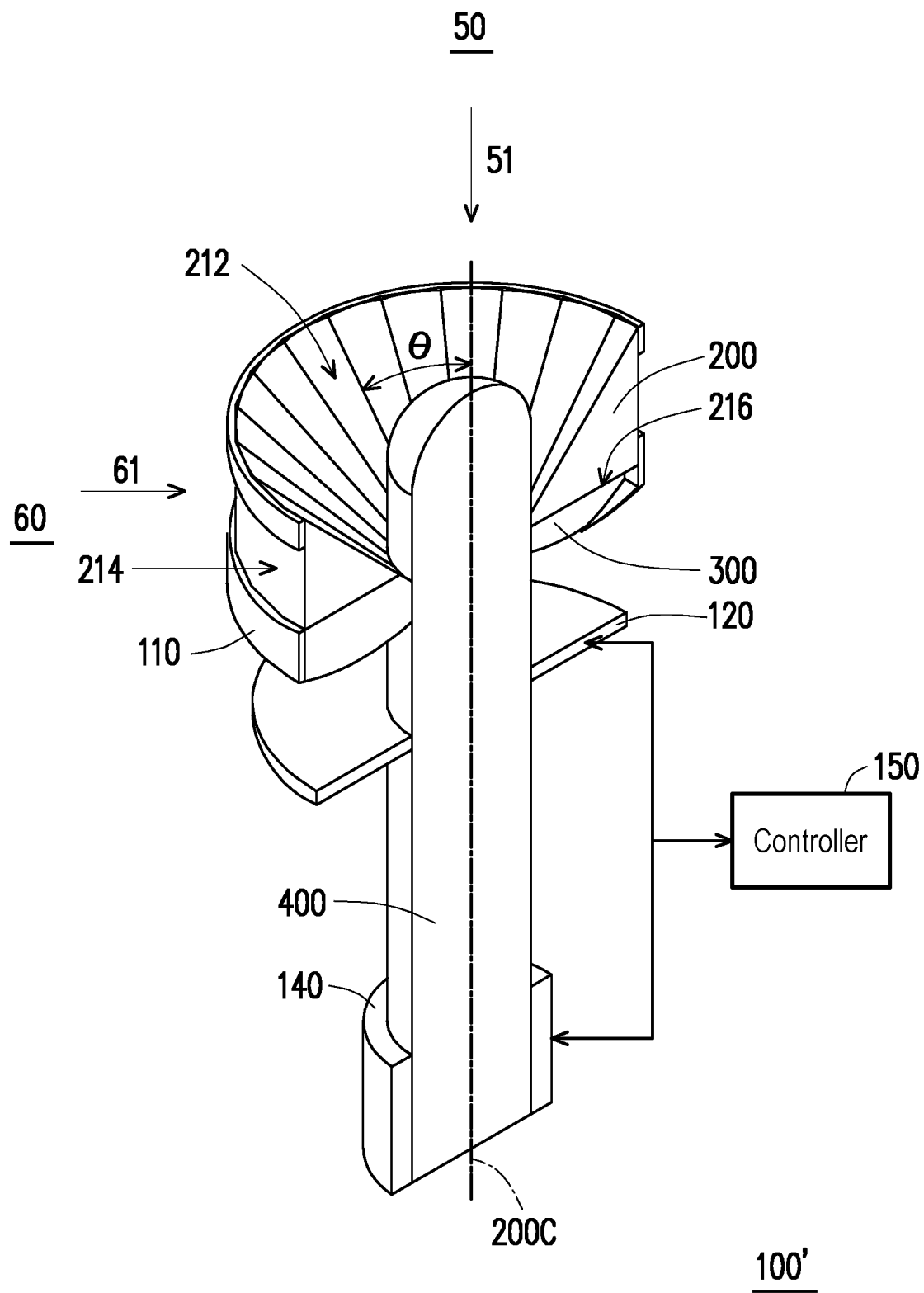
FIG. 3B is a schematic perspective view of the endoscope module of FIG. 3A cut along the central axis 200C.
Figure 3C:
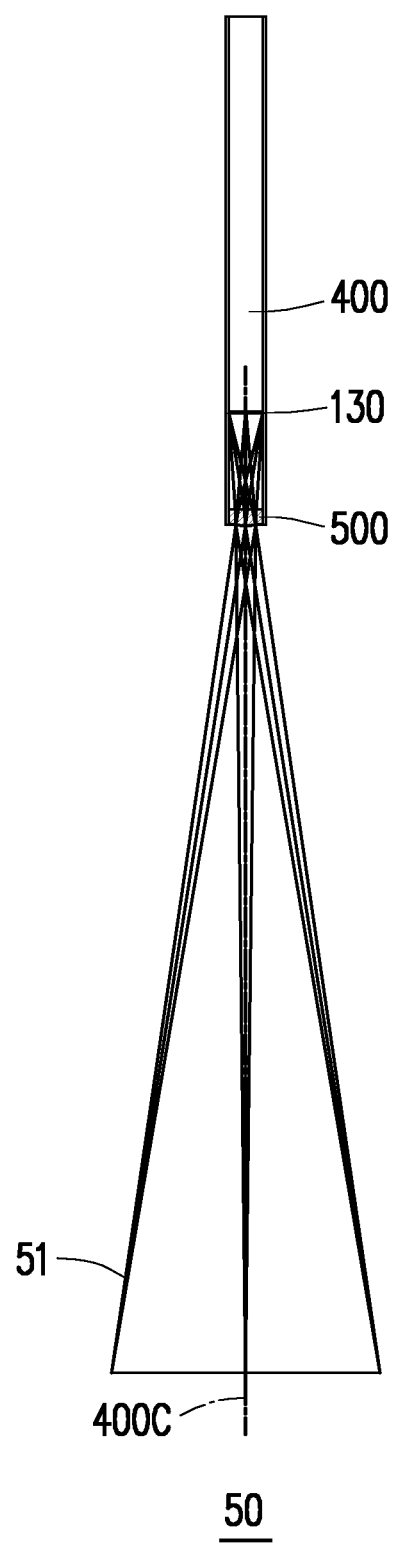
FIG. 3C is a schematic cross-sectional view of the inside of a fixing rod of an endoscope module according to an embodiment of the disclosure.
Figure 3D:
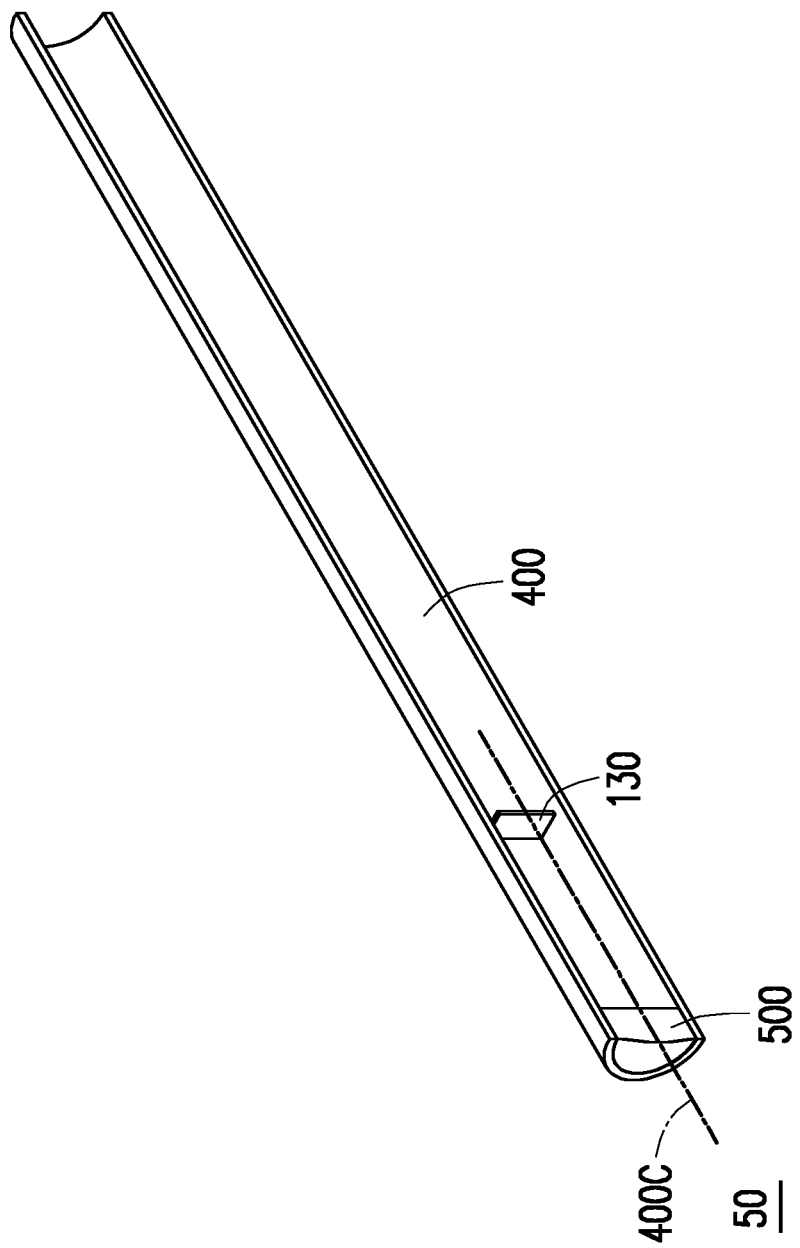
FIG. 3D is a schematic perspective view of the fixing rod of FIG. 3C cut along a central axis.

FIG. 3A is a schematic perspective view of an endoscope module provided with a fixing rod according to a second embodiment of the disclosure. FIG. 3B is a schematic perspective view of the endoscope module of FIG. 3A cut along the central axis 200C. FIG. 3C is a schematic cross-sectional view of the inside of a fixing rod of an endoscope module according to an embodiment of the disclosure. FIG. 3D is a schematic perspective view of the fixing rod of FIG. 3C cut along a central axis. With reference to FIG. 1B, FIG. 1C, FIG. 3A, FIG. 3B, FIG. 3C, and FIG. 3D together, an endoscope module 100' of FIG. 3A is similar to the endoscope module 100 of FIG. 1B, and is different in that the endoscope module 100' further includes a fixing rod 400. In this embodiment, the fixing rod 400 penetrates a center 200P, a center 300P, and the center 120P of the annular prism 200, the annular lens 300, and the annular image sensor 120 to fix the annular prism 200, the annular lens 300, and the annular image sensor 120. In this embodiment, openings O1, O2, and O3 are respectively present at the centers of the annular prism 200, the annular lens 300, and the annular image sensor 120 to be penetrated by the fixing rod 400.

In this embodiment, the endoscope module 100' further includes a lens 500 and an image sensor 130. The lens 500 and the image sensor 130 are both disposed in the fixing rod 400. The lens 500 and the image sensor 130 are disposed on the side of the fixing rod 400 close to the front surface 50. The frontal light 51 from the front surface 50 passes through the lens 500 and is transmitted to the image sensor 130.

In this embodiment, a focal length of the lens 500 is different from a focal length of the annular lens 300, but the disclosure is not limited thereto. In an embodiment, the focal length of the lens 500 may be the same as the focal length of the annular lens 300.

In addition, in FIG. 3A and FIG. 3D, the diameter of the lens 500 is about 1 mm, and the field angle of the endoscope module 100' on the front surface 50 is about 30 degrees (i.e., within a range of ±15 degrees). In the endoscope module 100' in the embodiment of the disclosure, since the lens 500 and the image sensor 130 are both disposed in the fixing rod 400, during manufacturing of the endoscope module 100', the optical alignment between the lens 500 and the image sensor 130 and the optical alignment between the annular prism 200, the annular lens 300, and the annular image sensor 120 do not affect each other, facilitating the process of optical alignment of the endoscope module 100'.

Figure 4:
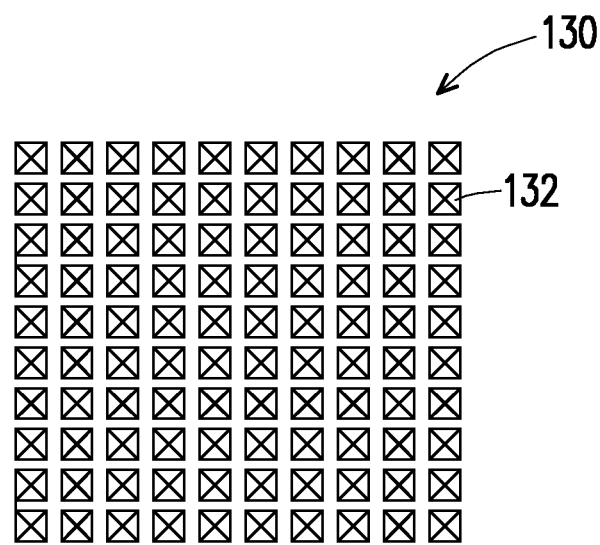
FIG. 4 is a schematic top view of an image sensor of an endoscope module according to an embodiment of the disclosure.

FIG. 4 is a schematic top view of an image sensor of an endoscope module according to an embodiment of the disclosure. With reference to FIG. 3C, FIG. 3D, and FIG. 4 together, in this embodiment, the image sensor 130 may be a light sensor of a complementary metal oxide semiconductor or a charge coupled device. The image sensor 130 has a plurality of second pixels 132. The second pixels 132 are arranged into an m×n matrix, where m≥2 and n≥2.

In addition, for convenience of illustration, only some of the second pixels 132 are shown in FIG. 4. In an embodiment, the second pixels 132 of the image sensor 130 are arranged into a 320×240 matrix, and the size of the image sensor 130 is about $(1/18)^2$ $inch^2$. Nonetheless, the disclosure is not limited thereto. The size of the image sensor 130 and the relationship between the elements may be determined depending on design requirements.

With reference to FIG. 1B, FIG. 1C, FIG. 3A, and FIG. 3B together, in this embodiment, the endoscope module 100 further includes a spinner 140 and a controller 150. The spinner 140 is connected to the fixing rod 400, and the spinner 140 is disposed on the side of the fixing rod 400 away from the front surface 50. The controller 150 is electrically connected to the spinner 140, the annular image sensor 120, and the image sensor 130.

In this embodiment, the spinner 140 is, for example, a rotating mechanism composed of a motor or a stepper motor.

In an embodiment, the controller 150 includes, for example, a central processing unit (CPU), a microprocessor, a digital signal processor (DSP), a programmable controller, a programmable logic device (PLD), or other similar devices or a combination of these devices, which is not limited by the disclosure. In addition, in an embodiment, the functions of the controller 150 may be implemented as programming codes. The program codes are stored in a memory unit and executed by the controller 150. Alternatively, in an embodiment, the functions of the controller 150 may be implemented as one or more circuits. It is not limited by the disclosure whether the functions of the controller 150 are implemented in software or hardware.

Figure 5:
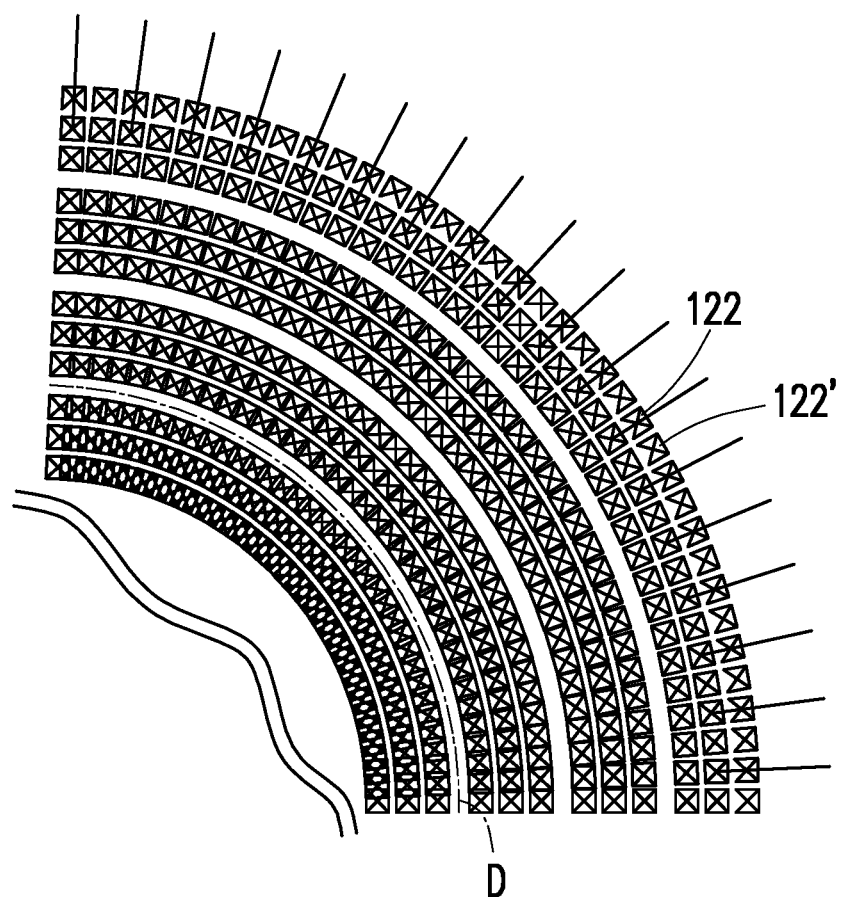
FIG. 5 is a schematic diagram of distribution of first pixels of an annular image sensor before and after a rotational movement.

FIG. 5 is a schematic diagram of distribution of first pixels of an annular image sensor before and after a rotational movement. The first pixels before the rotational movement are denoted as 122, and the first pixels after the rotational movement are denoted as 122'. With reference to FIG. 3A, FIG. 3B, FIG. 3C, FIG. 3D, and FIG. 5, in this embodiment, the controller 150 controls the spinner 140 to generate a rotational movement of the fixing rod 400 around a central axis 400C thereof. The controller 150 overlaps images obtained by the annular image sensor 120 during the rotational movement to increase the effective resolution of the endoscope module 100.

In an embodiment, the rotational movement is a vibration or a restoration after rotation.

Figure 6B:
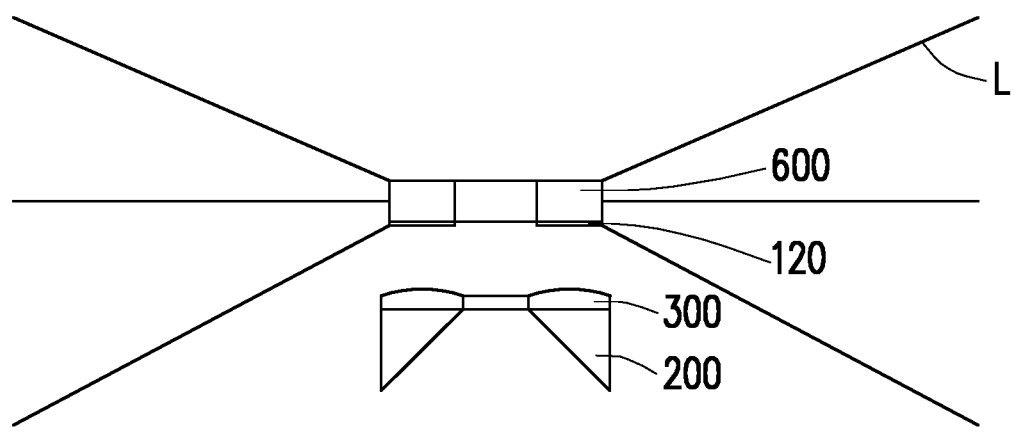
FIG. 6B is a schematic cross-sectional view of the endoscope module of FIG. 6A.

FIG. 6A is a perspective schematic view of an endoscope module according to a third embodiment of the disclosure cut along the central axis 200C. FIG. 6B is a schematic cross-sectional view of the endoscope module of FIG. 6A. With reference to FIG. 6A and FIG. 6B, an endoscope module 100" of FIG. 6A is similar to the endoscope module 100 of FIG. 1B, and is different in that the endoscope module 100" further includes the annular light source 600. In this embodiment, the annular light source 600 may be an annular light source formed by a plurality of edge-emitting light sources, and the light sources may be light-emitting diodes or other suitable light-emitting elements. The annular image sensor 120 is disposed between the annular light source 600 and the annular lens 300. The annular light source 600 emits an illumination light L. The illumination light L is reflected by the object to be detected to generate the frontal light 51 and the lateral light 61. In this embodiment, the annular light source 600 may alternately emit light in different colors, for example, alternately emitting a red light, a green light, and a blue light. Accordingly, the annular image sensor 120 or the image sensor 130 sequentially senses a red light image, a green light image, and a blue light image. After the controller 150 combines the red light image, the green light image, and the blue light image, a color image of the object to be detected around the endoscope module 100" may be obtained. In another embodiment, the annular light source 600 may emit infrared (IR) or short wave infrared (SWIR), where the infrared may be 940 nm and the short-wave infrared may be 1300 nm. Since infrared is suitable for detecting growth of new blood vessels under skin tissues, it may serve for detection of a potential precancerous lesion.

Figure 7:
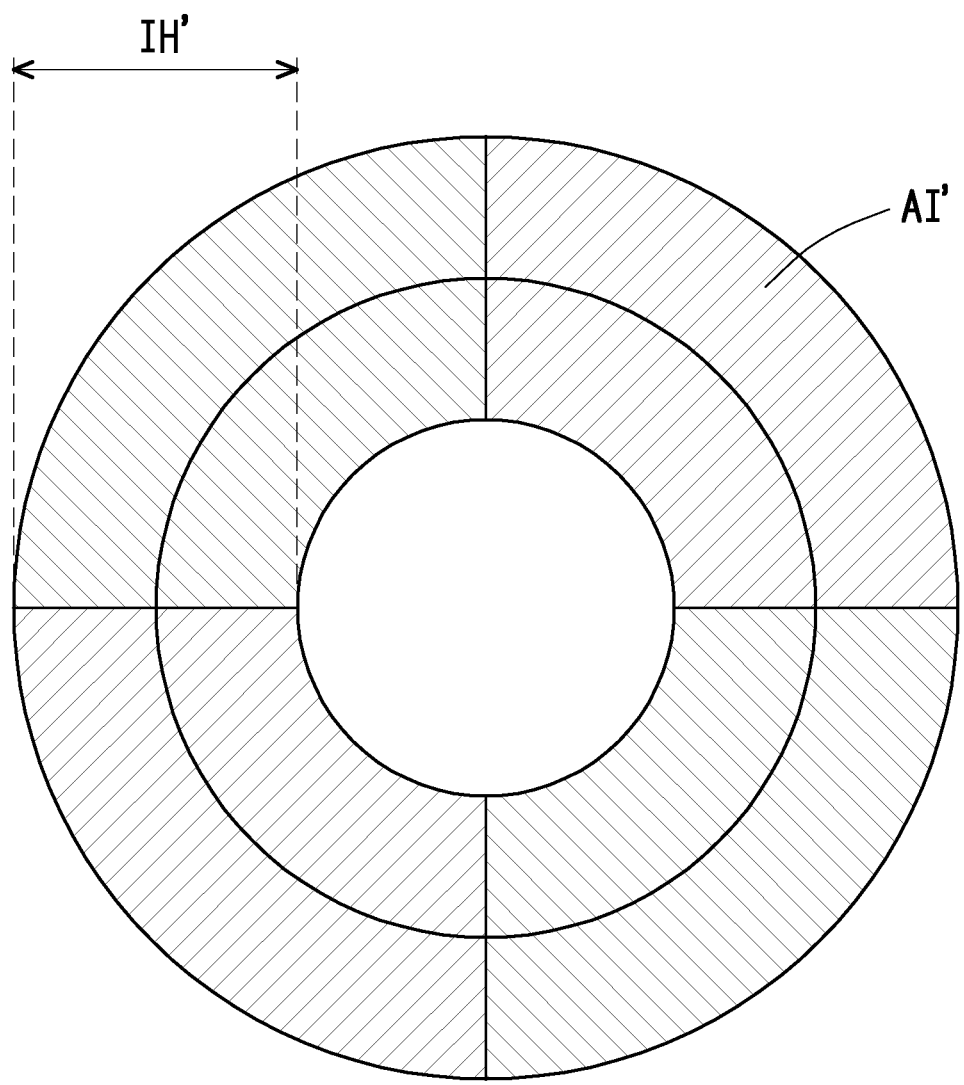
FIG. 7 is a schematic diagram of an annular image obtained by an annular image sensor.
Figure 8:
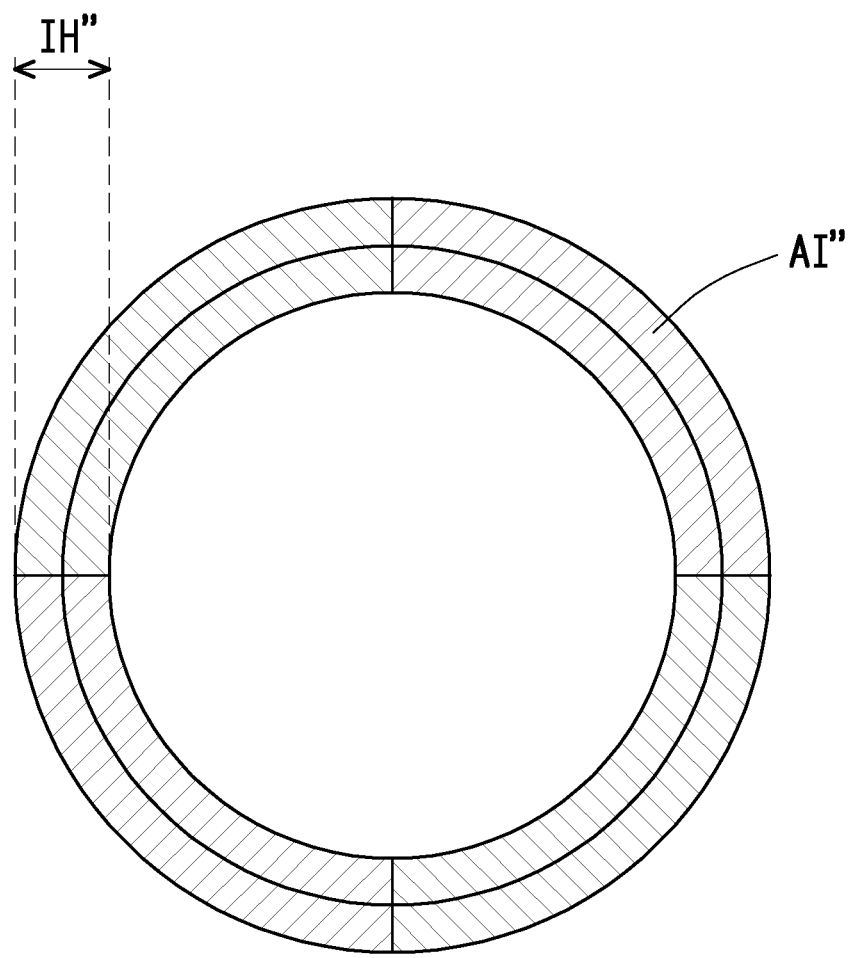
FIG. 8 is another schematic diagram of an annular image obtained by an annular image sensor.
Figure 9A:
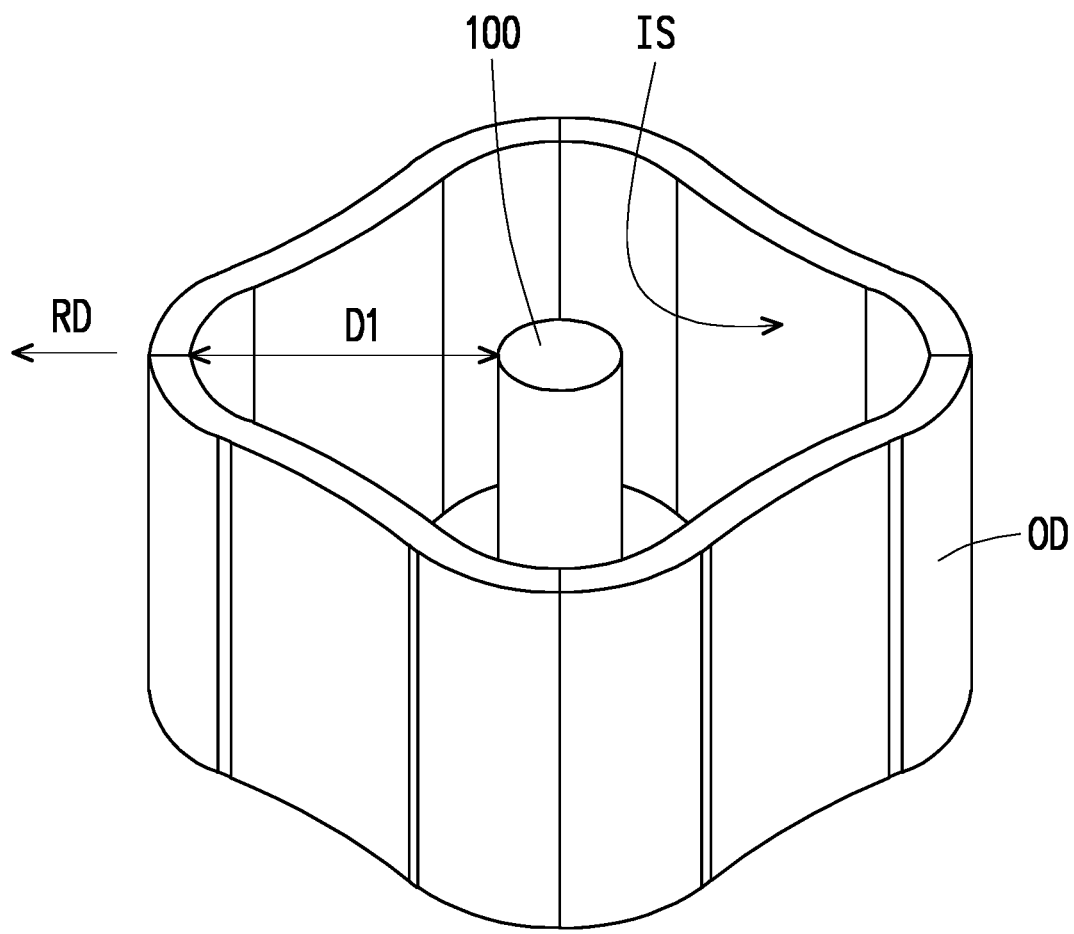
FIG. 9A is a diagram of application of an endoscope module according to an embodiment of the disclosure.
Figure 9B:
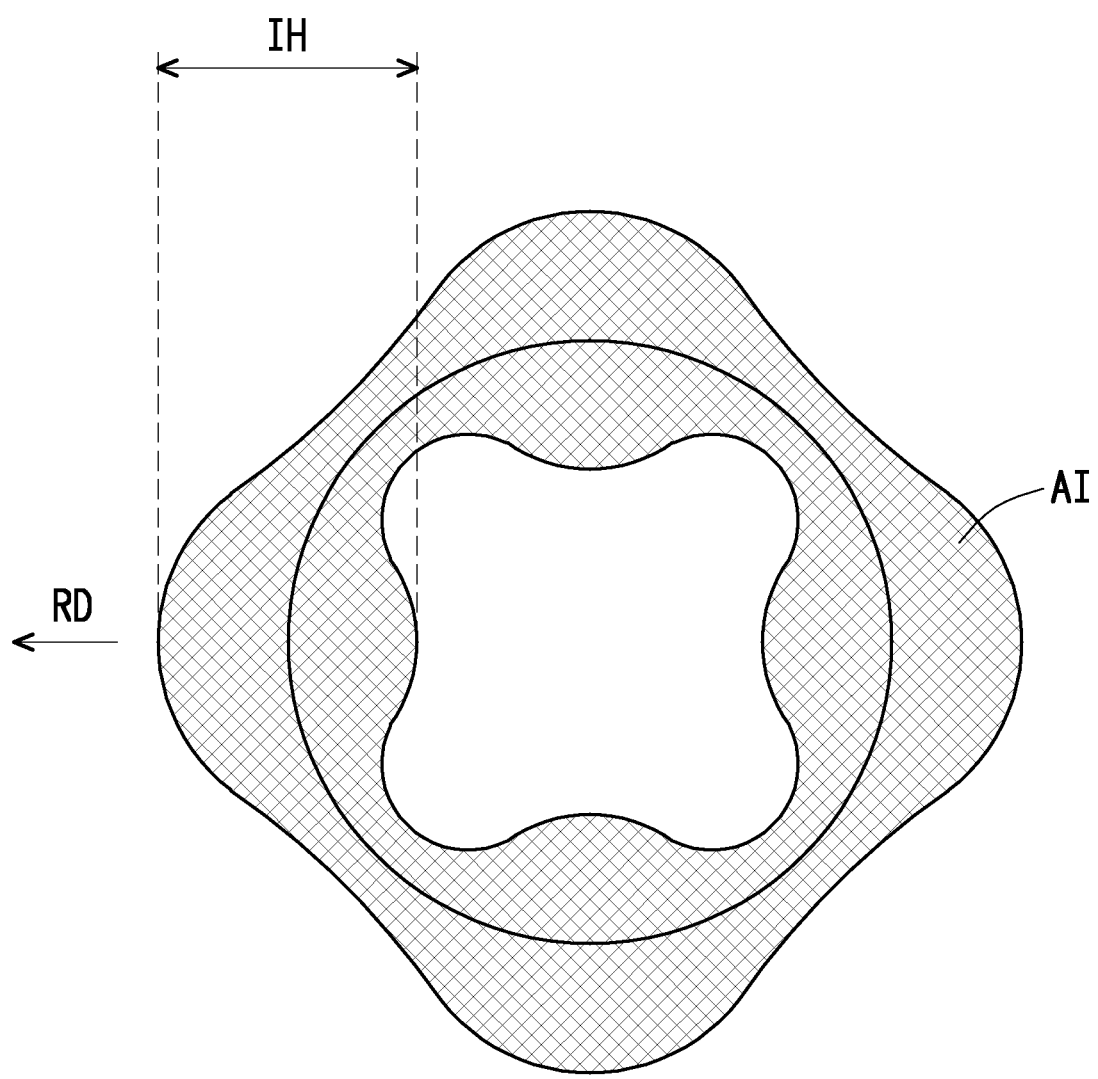
FIG. 9B is a schematic diagram of an annular image obtained by an annular image sensor in FIG. 9A.
Figure 9C:
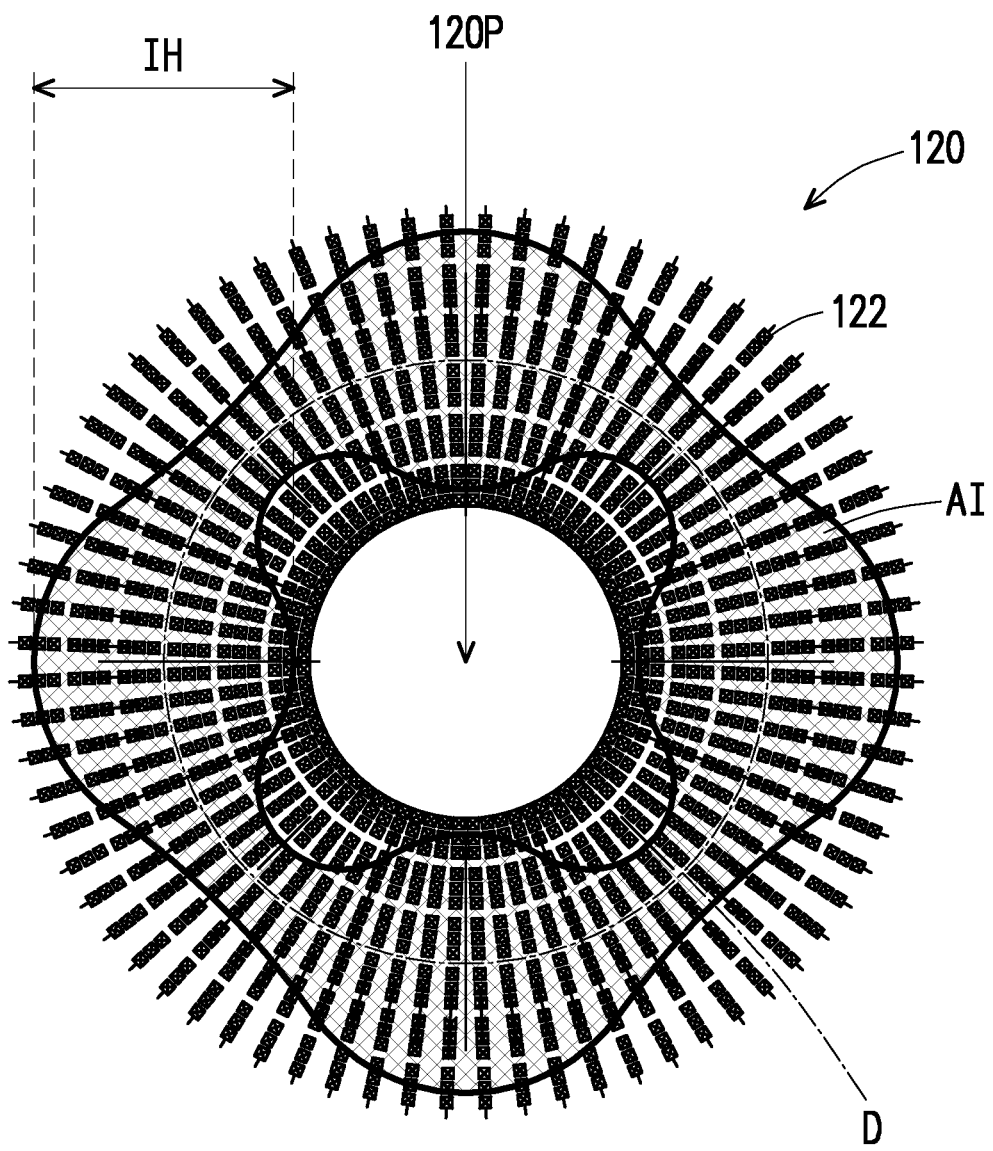
FIG. 9C is a schematic diagram of the annular image relative to first pixels of the annular image sensor of FIG. 9B.
Figure 9D:
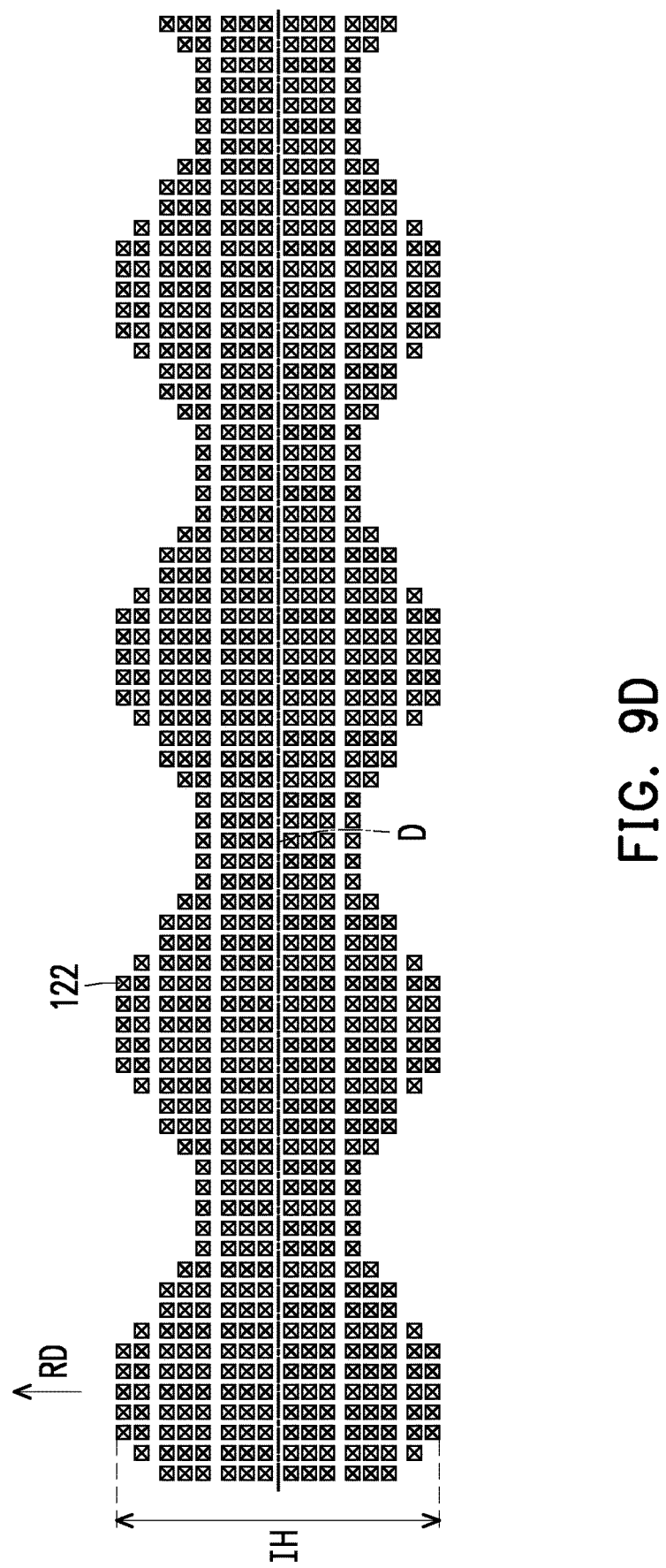
FIG. 9D is a schematic diagram of the first pixels within a distribution range of the annular image of FIG. 9C unfolded along the central segmentation line D.

FIG. 7 is a schematic diagram of an annular image obtained by an annular image sensor. FIG. 8 is another schematic diagram of an annular image obtained by an annular image sensor. FIG. 9A is a diagram of application of an endoscope module according to an embodiment of the disclosure. FIG. 9B is a schematic diagram of an annular image obtained by an annular image sensor in FIG. 9A. FIG. 9C is a schematic diagram of the annular image relative to first pixels of the annular image sensor of FIG. 9B. FIG. 9D is a schematic diagram of the first pixels within a distribution range of the annular image of FIG. 9C unfolded along the central segmentation line D.

In addition, in this embodiment, an image of an object to be detected OD obtained by the annular image sensor 120 is an annular image AI. In any radial direction RD starting from the center 120P of the annular image sensor 120, an image height IH of the annular image AI in the radial direction RD is proportional to a distance D1 between (an inner surface IS of) the object to be detected OD and the endoscope module 100 in the radial direction RD. In the meanwhile, the distance D1 also reflects the depth value of the object to be detected OD in the radial direction RD.

To be specific, formula (1) is the thin lens equation $$\frac{1}{p} + \frac{1}{q} = \frac{1}{f} \quad (1)$$

where p is the object distance, q is the image distance, and f is the focal length. The optical values such as the object distance p and the image distance q in formula (1) are obtained by the endoscope module 100 in the radial direction RD, for example. Similarly, considering the annular image AI in another radial direction, formula (2) can be obtained as follows $$\frac{1}{p+\Delta p} + \frac{1}{q+\Delta q} = \frac{1}{f} \quad (2)$$

Then, by defining the magnification ratio M=p/q and M'=(p+Δp)/(q−Δq), formulae (1) and (2) can be respectively calculated to derive $$1 + M = \frac{p}{f}$$

$$1 + M' = \frac{p + \Delta p}{f}$$

Since M'−M=Δp/f, formulae (3) and (4) can be further obtained $$\Delta p = f \Delta M \quad (3)$$

$$f = \frac{\Delta p}{\Delta M} \quad (4)$$

where ΔM=M'−M. In other words, the difference value of the object distance Δp is proportional to the difference value of the magnification ratio ΔM. Since the object distance p reflects the distance D1 between the inner surface IS of the object to be detected OD and the endoscope module 100 in the radial direction RD and the magnification ratio M reflects the image height IH, by calculating the image height IH of the annular image AI in each radial direction RD, detecting personnel may then calculate the distance D1 between the inner surface IS of the object to be detected OD and the endoscope module 100. Moreover, since the distance D1 reflects the depth value of the object to be detected OD in the radial direction RD, detecting personnel may construct the three-dimensional structure of the object to be detected OD based on the image height IH.

In addition, considering that the range of the depth value is within 10 millimeters (mm), and the difference value of the magnification ratio ΔM is about 2, the annular lens 300 of the endoscope module 100 in the embodiment of the disclosure should be designed with a focal length f of about 5 mm.

Reference may be made to FIG. 7 and FIG. 8, which respectively show similar annular images AI' and AI". Since an image height of the annular image AI' is greater than an image height IH" of the annular image AI", and based on the relationship between formula (1) to formula (4) above, the corresponding depth value of the object to be detected OD in FIG. 7 is greater than the corresponding depth value of the object to be detected OD in FIG. 8.

With reference to FIG. 9A to FIG. 9D, in which the relationship between the image height IH and the distance D1 and the reflection of the depth value of the object to be detected OD by the image height IH have been described in detail in formulae (1) to (4) above, and will not be repeated herein. Furthermore, FIG. 9D is a schematic diagram of the first pixels 122 within the distribution range of the annular image AI of FIG. 9C unfolded along the central segmentation line D. In FIG. 9C, the number of first pixels 122 within the range from the center 120P to the central segmentation line D is the same as the number of first pixels 122 within the range beyond the central segmentation line D in the direction away from the center 120P. In FIG. 9D, the number of first pixels 122 above the central segmentation line D is the same as the number of first pixels 122 below the central segmentation line D.

Figure 10A:
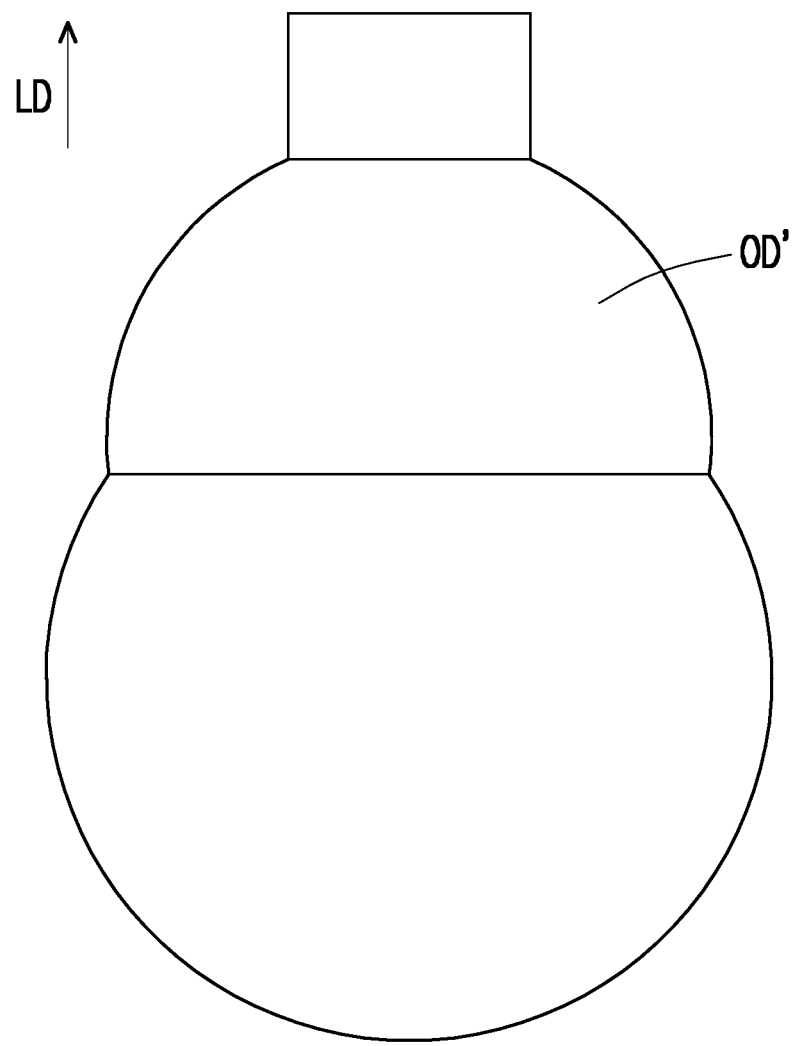
FIG. 10A is an exemplary perspective diagram of an object to be detected.
Figure 10B:
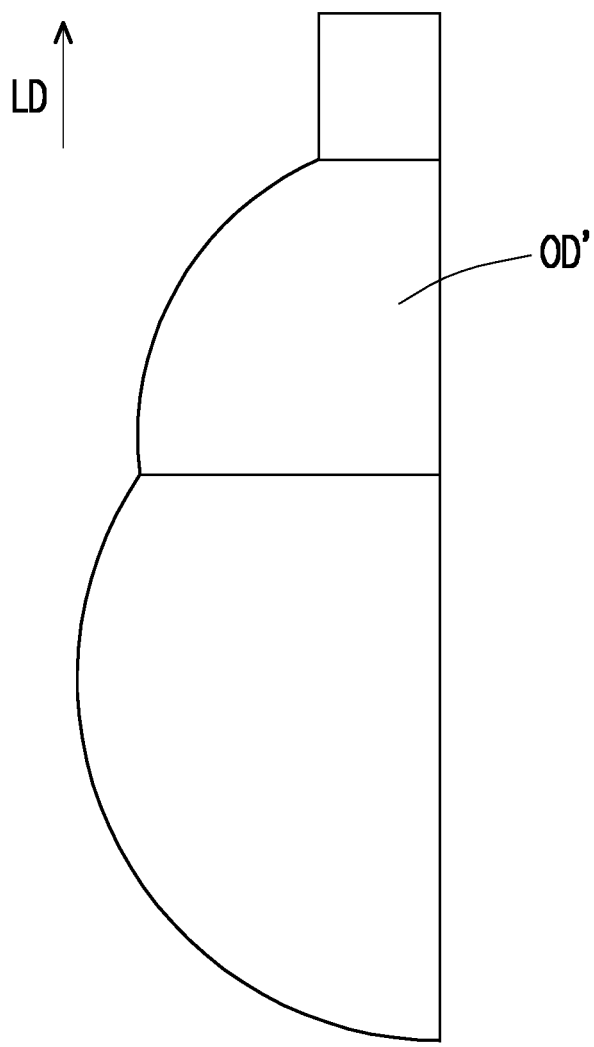
FIG. 10B is a schematic perspective view of the object to be detected of FIG. 10A cut along a longitudinal direction LD.
Figure 10C:
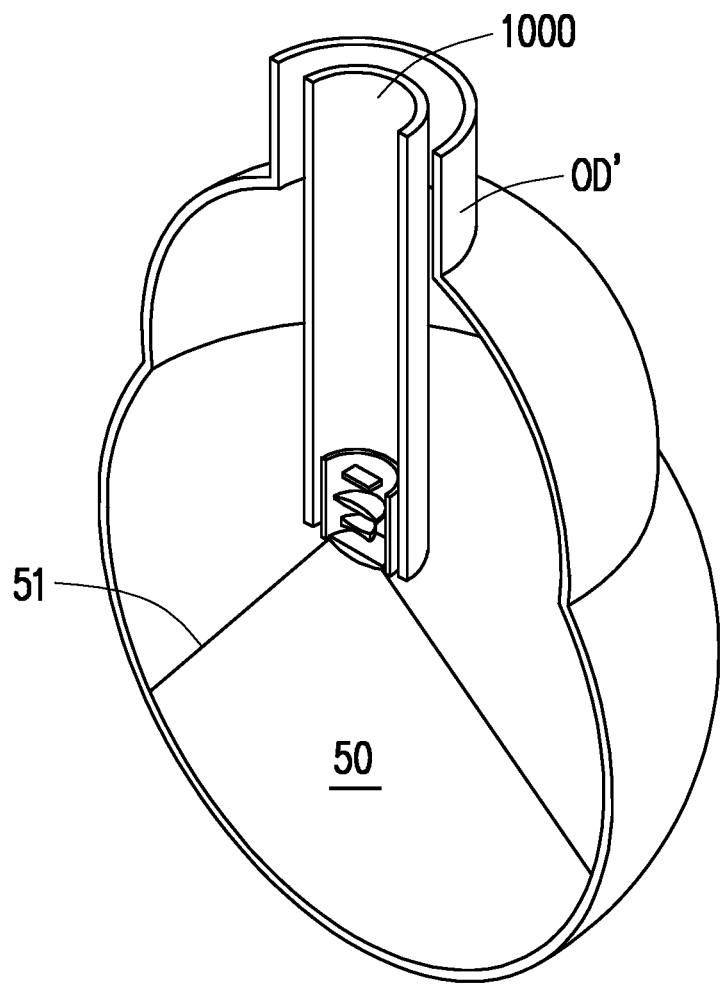
FIG. 10C is a schematic diagram of the object to be detected of FIG. 10B being detected by an endoscope module according to an exemplary embodiment.
Figure 10D:
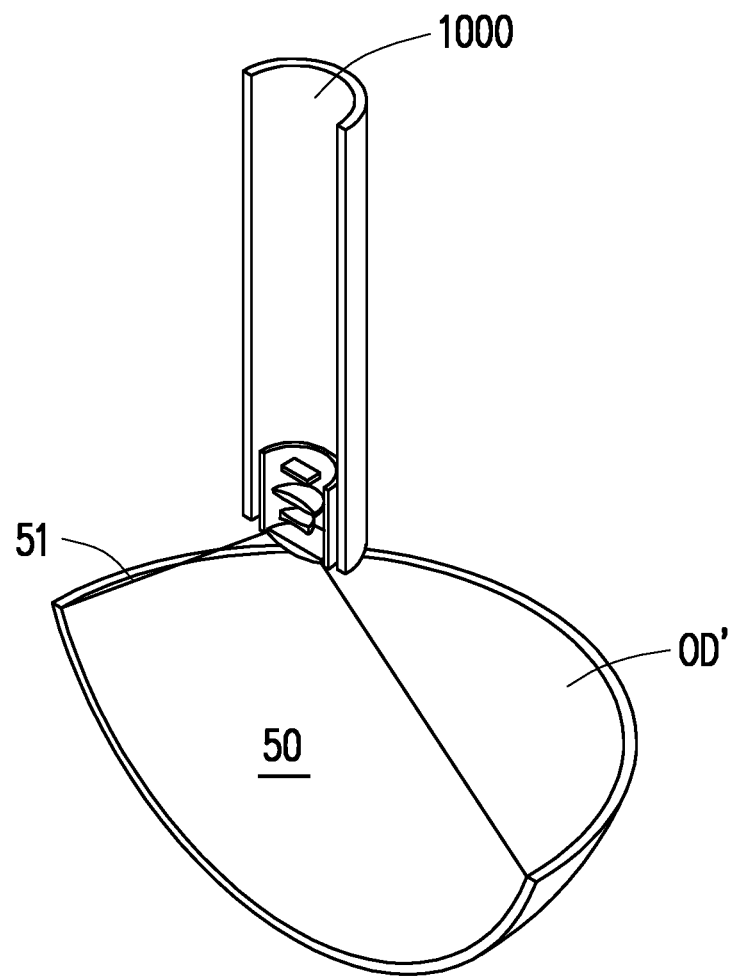
FIG. 10D is a schematic diagram of a detectable range of the endoscope module of the exemplary embodiment in FIG. 10C.

FIG. 10A is an exemplary perspective diagram of an object to be detected. FIG. 10B is a schematic perspective view of the object to be detected of FIG. 10A cut along a longitudinal direction LD. FIG. 10C is a schematic diagram of the object to be detected of FIG. 10B being detected by an endoscope module according to an exemplary embodiment. FIG. 10D is a schematic diagram of a detectable range of the endoscope module of the exemplary embodiment in FIG. 10C. With reference to FIG. 10A to FIG. 10D together, in FIG. 10A to FIG. 10D, since an endoscope module 1000 of the exemplary embodiment can only detect the frontal light 51 from the front surface 50, the detectable range of the endoscope module 1000 is limited to a part of an object to be detected OD' as shown in FIG. 10D. For the other parts of the object to be detected OD', as shown in FIG. 10A to FIG. 10C, the endoscope module 1000 cannot complete the scanning in one detection. In contrast, as shown in FIG. 1B to FIG. 1C, since the endoscope module 100 in an embodiment of the disclosure includes the annular prism 200, the annular lens 300, and the annular image sensor 120, the endoscope module 100 may obtain the lateral light 61 from the side surface 60. Accordingly, the endoscope module 100 may obtain the image of the side surface of the object to be detected OD. Furthermore, as shown in FIG. 3A to FIG. 3D, since the endoscope module 100 further includes the lens 500 and the image sensor 130, the endoscope module 100 may also obtain the frontal light 51 from the front surface 50. Accordingly, the endoscope module 100 obtains the images of the object to be detected OD from the front surface and the side surface at the same time.

Figure 11A:
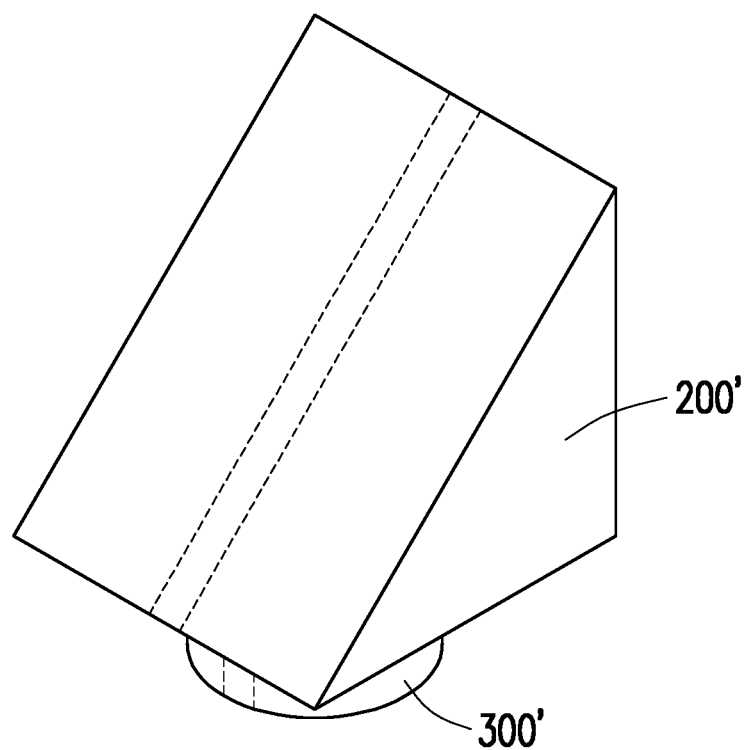
FIG. 11A is a conceptual diagram of an endoscope module according to another exemplary embodiment.
Figure 11A:
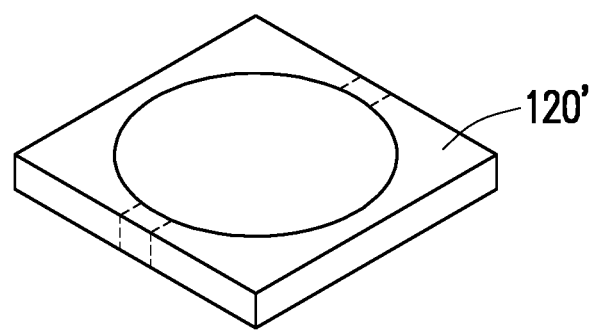
Figure 11B:
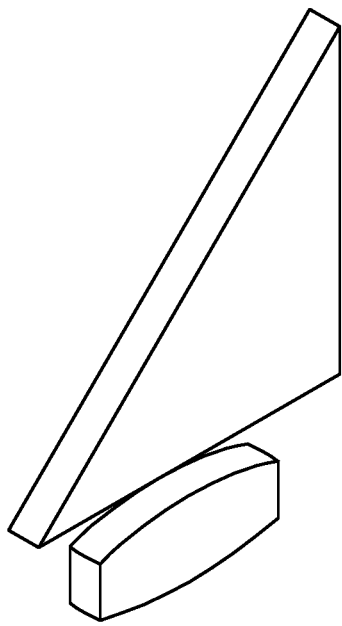
FIG. 11B is a schematic perspective view of a slice of the endoscope module of FIG. 11A.
Figure 11B:
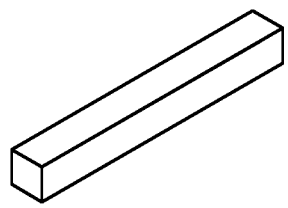
Figure 11C:
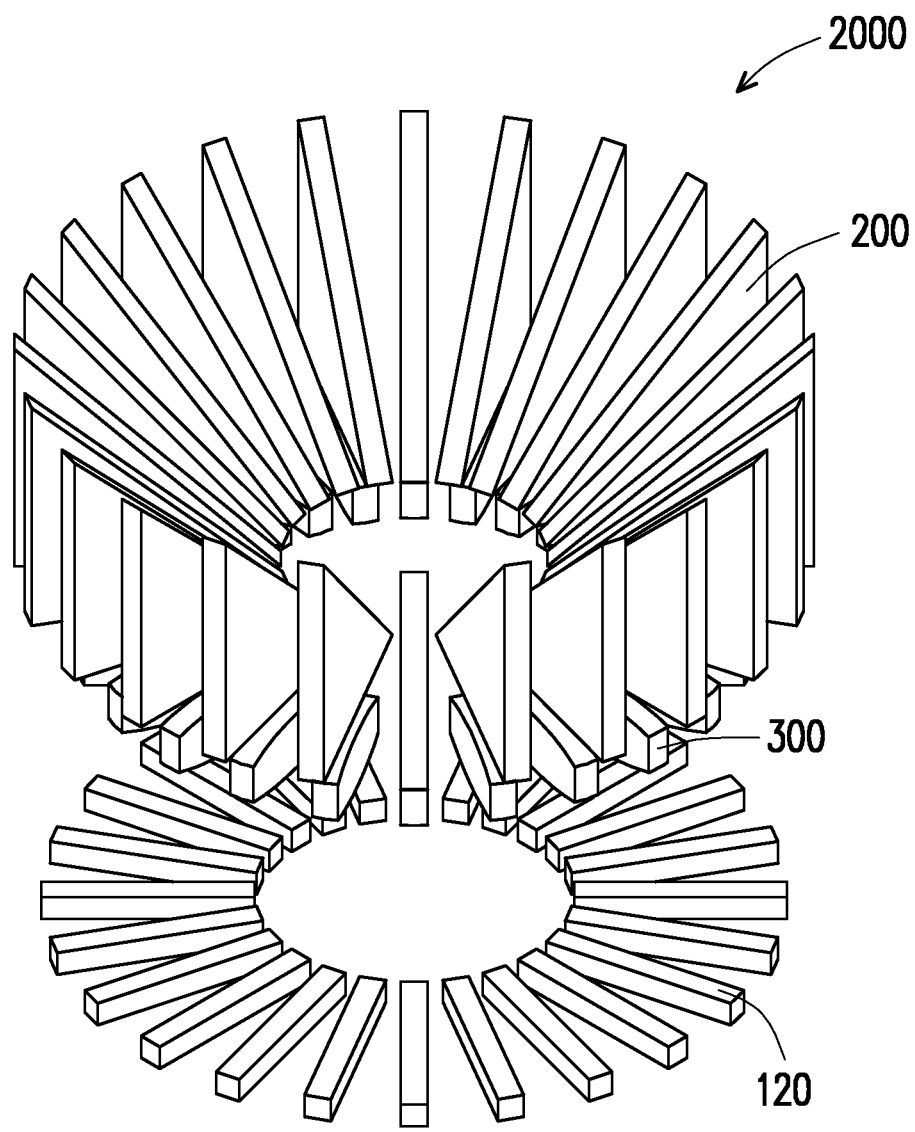
FIG. 11C is a schematic perspective view of an annular arrangement of a plurality of the structures of FIG. 11B.
Figure 11D:
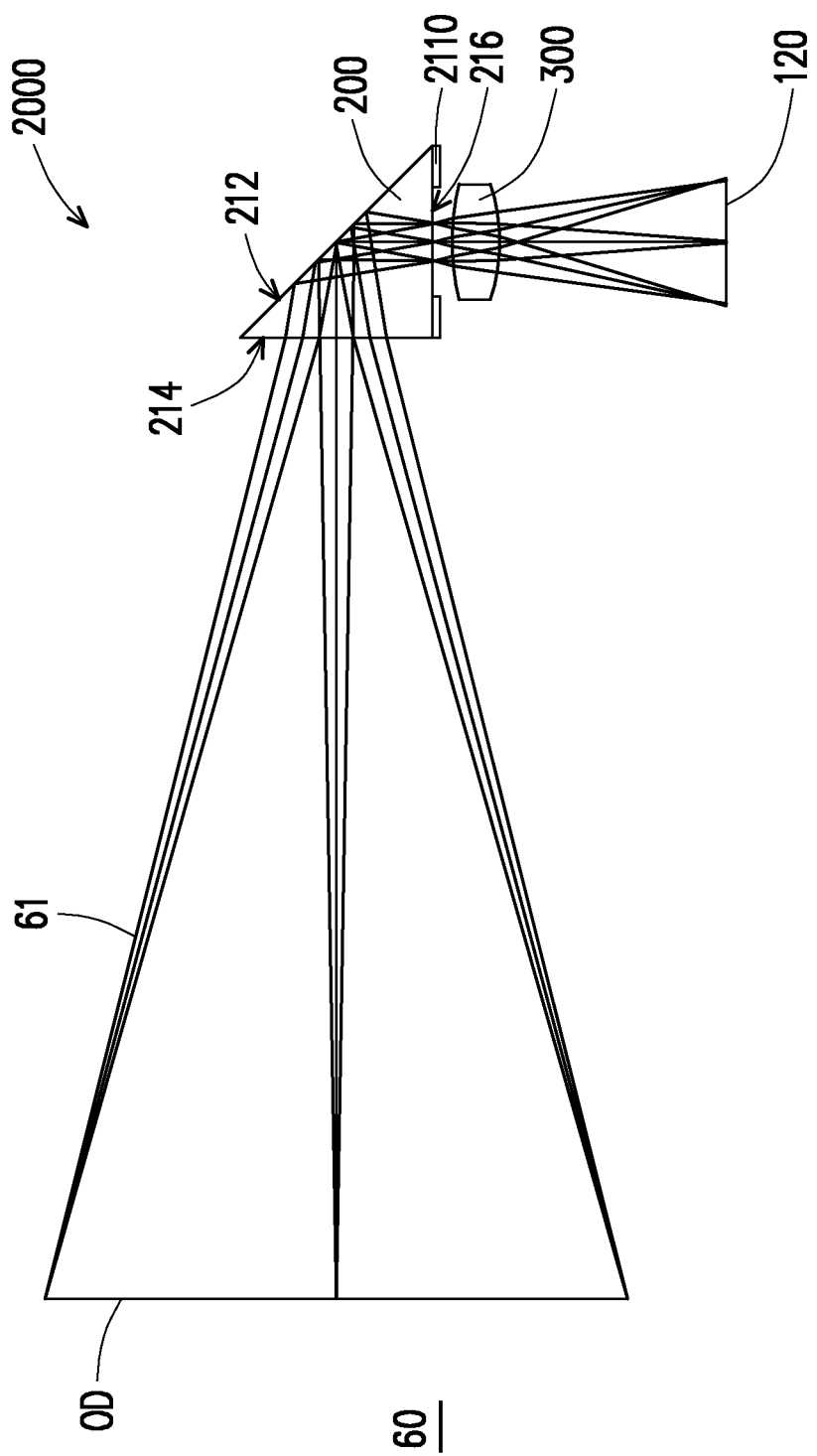
FIG. 11D is a schematic diagram of reception of a lateral light from a side by an endoscope module of an exemplary embodiment formed by combining the structures of FIG. 11C.

FIG. 11A is a conceptual diagram of an endoscope module according to another exemplary embodiment. FIG. 11B is a schematic perspective view of a slice of the endoscope module of FIG. 11A. FIG. 11C is a schematic perspective view of an annular arrangement of a plurality of the structures of FIG. 11B. FIG. 11D is a schematic diagram of reception of a lateral light from a side by an endoscope module of an exemplary embodiment formed by combining the structures of FIG. 11C. An endoscope module 2000 of the exemplary embodiment of FIG. 11D is generally the same as the endoscope module 100 of FIG. 1B, and is mainly different in that an annular stop 2110 of the endoscope module 2000 is disposed on the side of the light emitting surface 216 of the annular prism 200.

Figure 12:
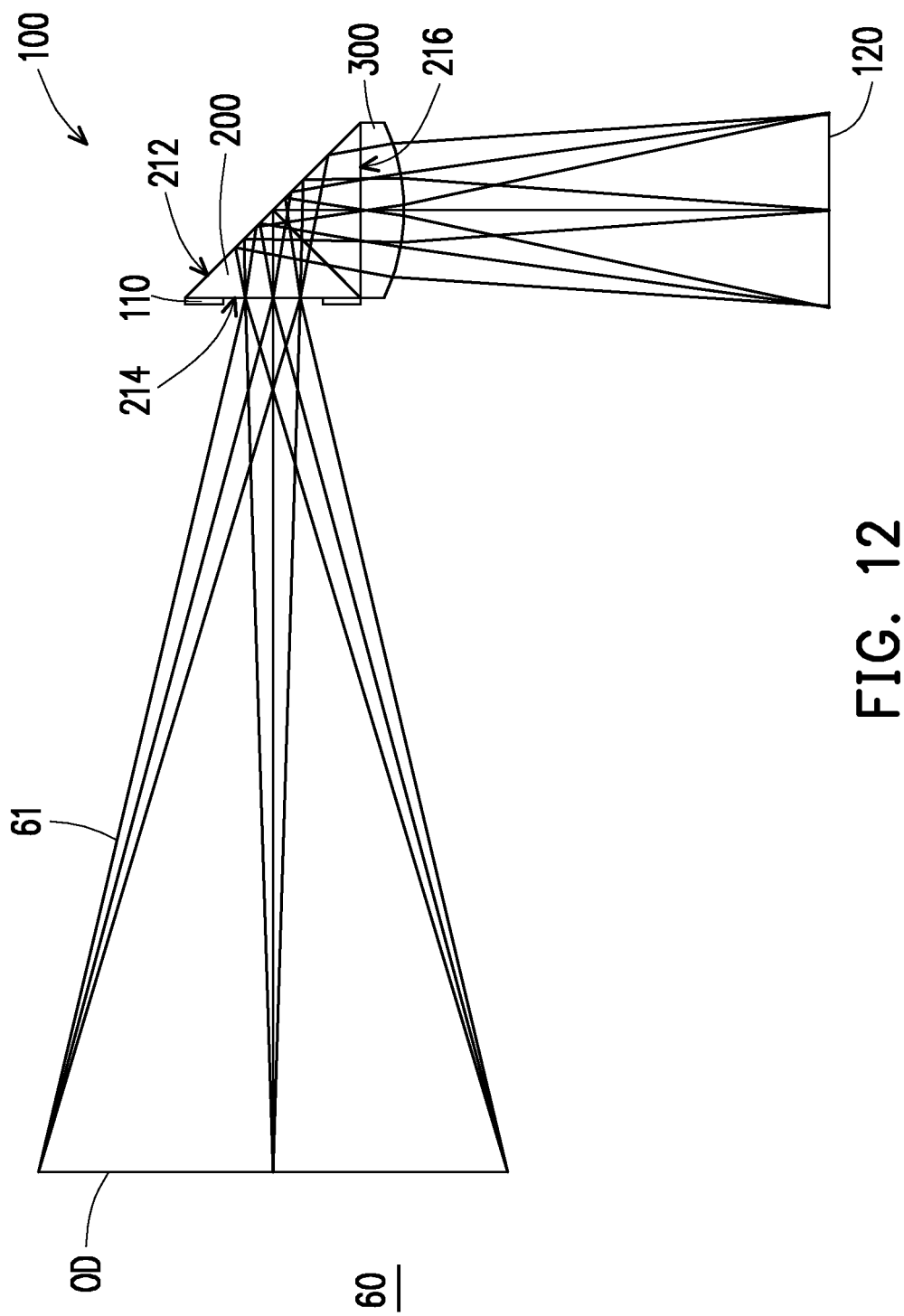
FIG. 12 is a schematic diagram of reception of a lateral light from a side by an endoscope module according to an embodiment of the disclosure.

FIG. 12 is a schematic diagram of reception of a lateral light from a side by an endoscope module according to an embodiment of the disclosure. With reference to FIG. 11D and FIG. 12 together, in the endoscope module 100 of an embodiment of the disclosure, since the annular prism 200 and the annular lens 300 are adopted to transmit the lateral light 61 from the side surface 60 to the annular image sensor 120, the endoscope module 100 may sense the image of the object to be detected OD on the side surface 60. Furthermore, compared to the annular stop 2110 of the endoscope module 2000 disposed on the side of the light emitting surface 216 of the annular prism 200, since the annular stop 110 is disposed on the side of the light incident surface 214 of the annular prism 200, the endoscope module 100 in the embodiment of the disclosure is more helpful in reducing the distance between the annular prism 200 and the annular lens 300, further reducing the overall volume of the endoscope module 100.

Figure 13A:
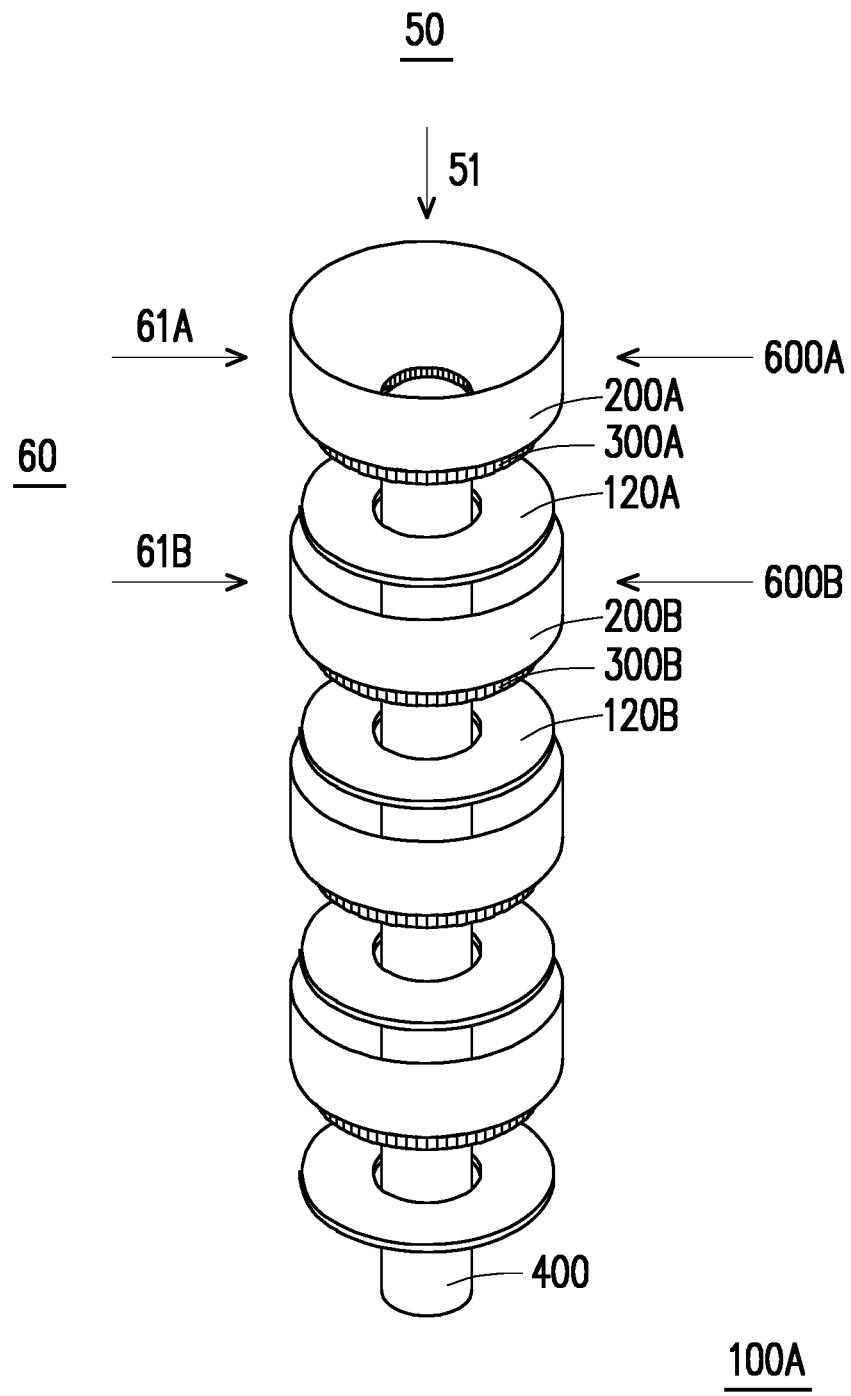
FIG. 13A is a schematic perspective view of an endoscope module according to a fourth embodiment of the disclosure.
Figure 13B:
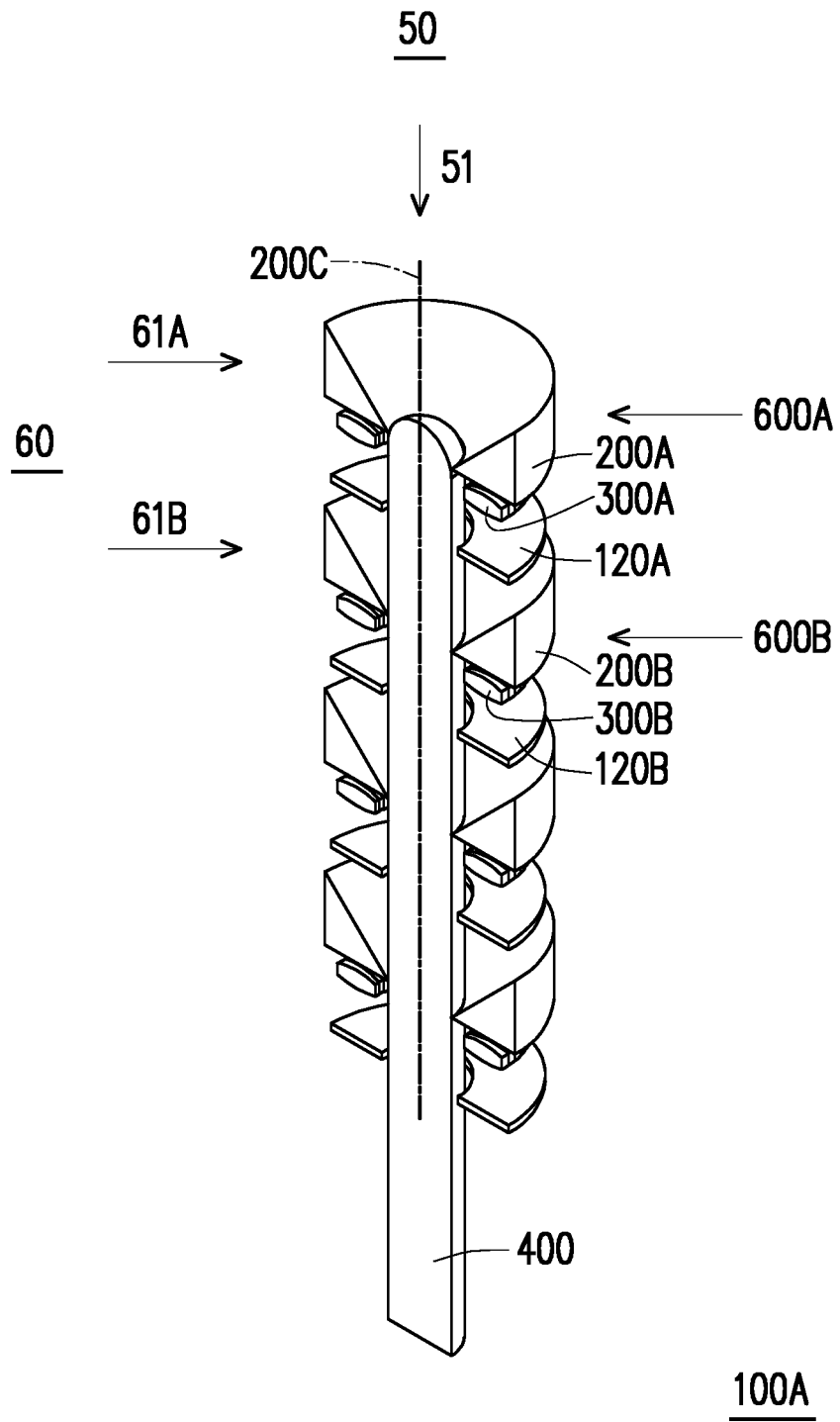
FIG. 13B is a schematic perspective view of the endoscope module of FIG. 13A cut along the central axis 200C.

FIG. 13A is a schematic perspective view of an endoscope module according to a fourth embodiment of the disclosure. FIG. 13B is a schematic perspective view of the endoscope module of FIG. 13A cut along the central axis 200C. With reference to FIG. 13A and FIG. 13B together, an endoscope module 100A of this embodiment is similar to the endoscope module 100 of FIG. 1B, and the difference between them is described as follows. The endoscope module 100A of the embodiment includes a first sub-endoscope module 600A and at least one second sub-endoscope module 600B. The first sub-endoscope module 600A is the same as the endoscope module 100 of FIG. 1B, and includes a first annular prism 200A, a first annular lens 300A, a first annular stop 110A, and a first annular image sensor 120A. The specifics of the elements and their relationships have been described in detail in the foregoing embodiments, and will not be repeatedly described herein. Moreover, the light path where a first lateral light 61A is transmitted to the first annular image sensor 120A is also the same as the light path where the lateral light 61 is transmitted to the annular image sensor 120, and will not be repeatedly described herein.

Furthermore, in this embodiment, the second sub-endoscope module 600B is disposed on a side of the first sub-endoscope module 600A. Each second sub-endoscope module 600B is the same as the endoscope module 100 of FIG. 1B, and includes a second annular prism 200B, a second annular lens 300B, a second annular stop 110B, and a second annular image sensor 120B. The specifics of the elements and their relationship have been described in detail in the foregoing embodiments, and will not be repeatedly described herein. Moreover, the light path where a second lateral light 61B is transmitted to the second annular image sensor 120B is also the same as the light path where the lateral light 61 is transmitted to the annular image sensor 120, and will not be repeatedly described herein.

Figure 14:
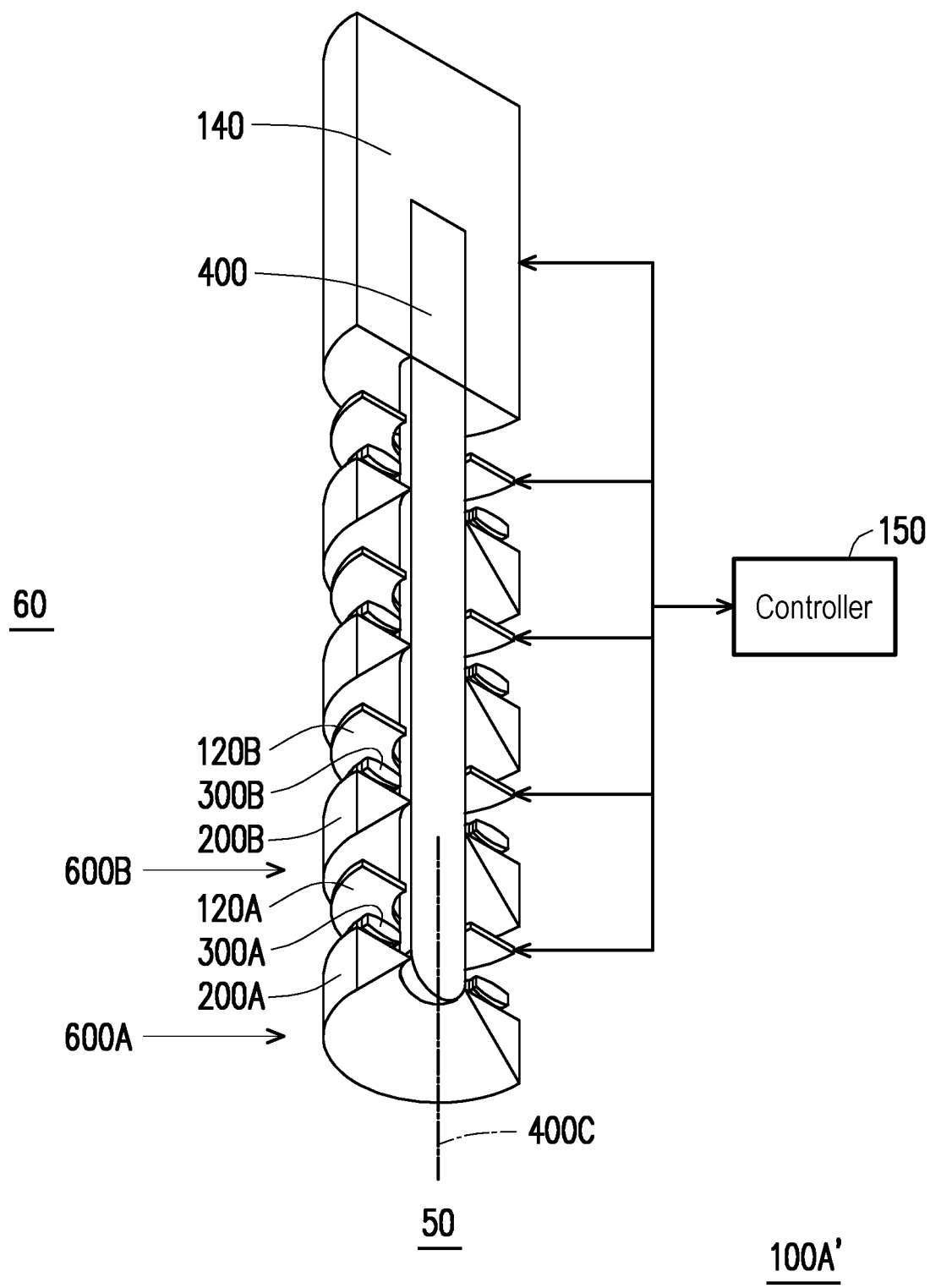
FIG. 14 is a schematic perspective view of an endoscope module provided with a spinner and a controller according to a fifth embodiment of the disclosure.

FIG. 14 is a schematic perspective view of an endoscope module provided with a spinner and a controller according to a fifth embodiment of the disclosure. An endoscope module 100A' of this embodiment is similar to the endoscope module 100' of FIG. 3A. In addition, the specifics of the endoscope module 100A' provided with the spinner 140 and the controller 150 and the relationship between the elements have been described in detail in the foregoing embodiments, and will not be repeatedly described herein.

Figure 15A:
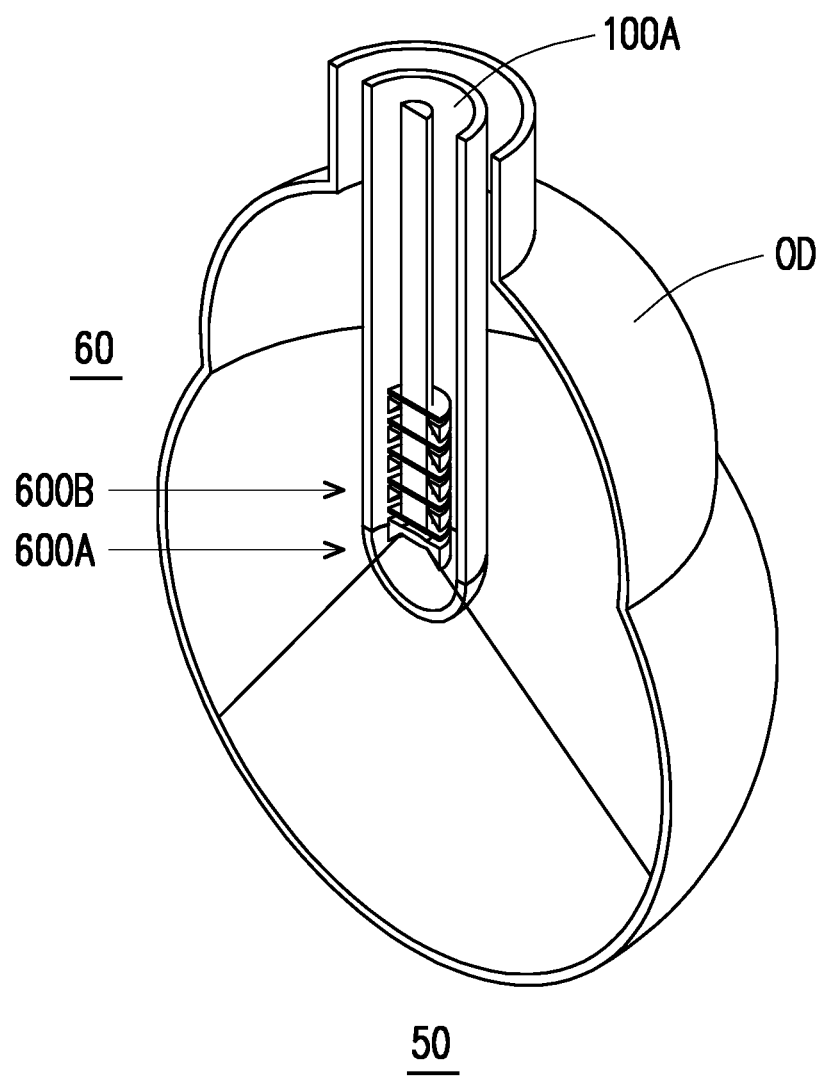
FIG. 15A is a schematic diagram of application of the endoscope module of the fourth embodiment of the disclosure.
Figure 15B:
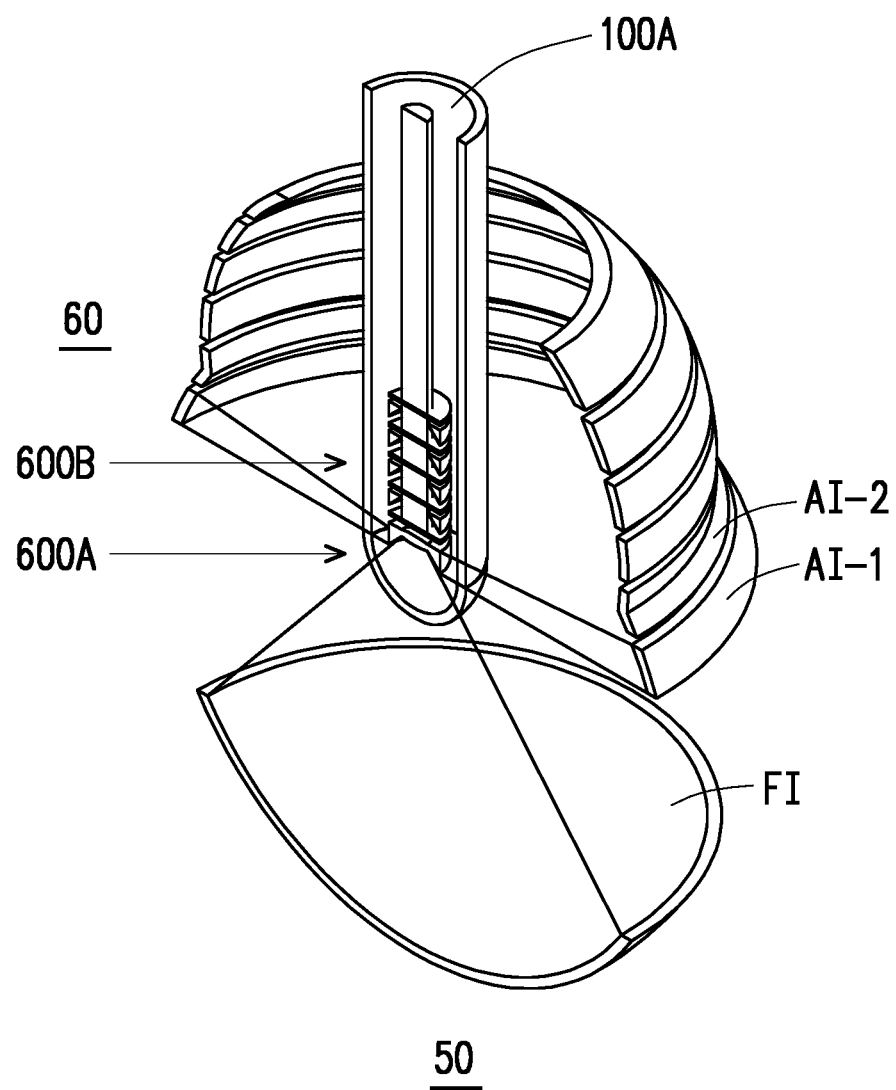
FIG. 15B is a schematic diagram of an annular image sensor in FIG. 15A obtaining an annular image and a frontal image.
Figure 15C:
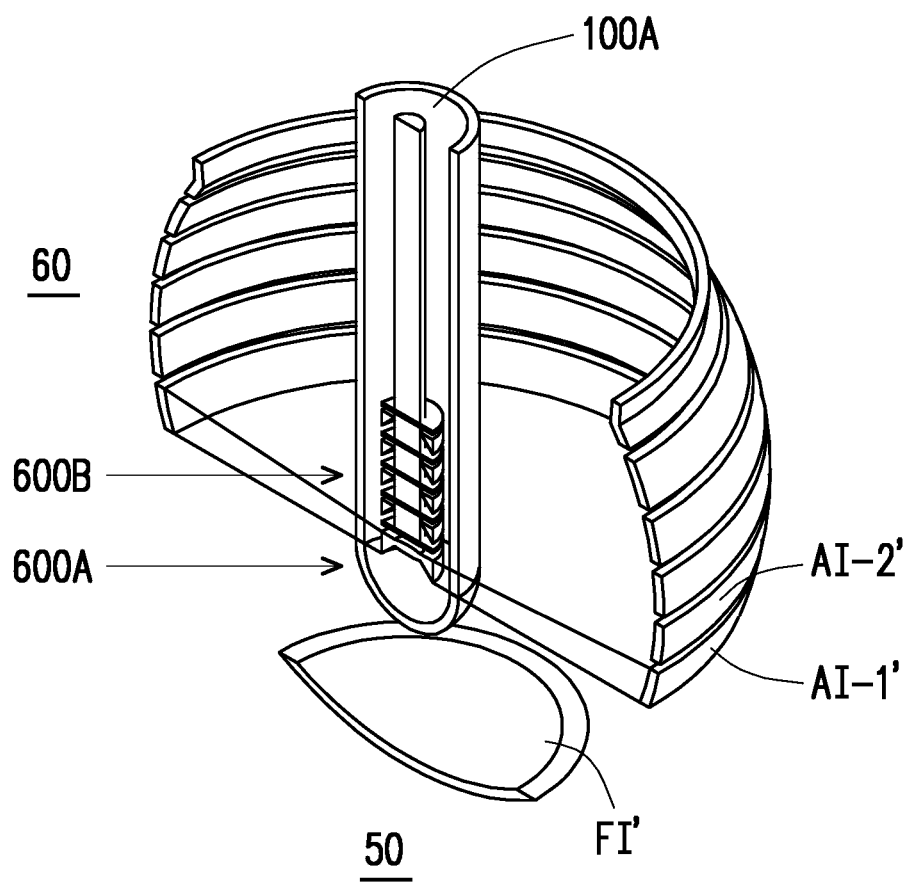
FIG. 15C is another schematic diagram of the annular image sensor in FIG. 15A obtaining an annular image and a frontal image at positions different from those of FIG. 15B.

FIG. 15A is a schematic diagram of application of the endoscope module of the fourth embodiment of the disclosure. FIG. 15B is a schematic diagram of an annular image sensor in FIG. 15A obtaining an annular image and a frontal image. FIG. 15C is another schematic diagram of the annular image sensor in FIG. 15A obtaining an annular image and a frontal image at positions different from those of FIG. 15B. With reference to FIG. 15A to FIG. 15C together, in the embodiment of the disclosure, since the endoscope module 100A includes the first sub-endoscope module 600A and the at least one second sub-endoscope module 600B, the endoscope module 100A may not only obtain first annular images AI-1, AI-1' with the first sub-endoscope module 600A, but also obtain second annular images AI-2, AI-2' with the second sub-endoscope module 600B, such that the endoscope module 100A can complete the scanning of the object to be detected OD within a shorter time, effectively reducing the detection time.

In addition, when the endoscope module 100A of the embodiment of the disclosure is also provided with the lens 500 and the image sensor 130 of FIG. 3C in the fixing rod 400, the endoscope module 100A may not only obtain the first annular images AI-1, AI-1' and the second annular images AI-2, AI-2' from the side surface 60, but also obtain frontal images FI, FI' from the front surface 50. Therefore, the endoscope module 100A may sense objects on the front surface 50 and the side surface 60 at the same time.

In summary of the foregoing, in the endoscope module of an embodiment of the disclosure, since the annular prism and the annular lens are adopted to transmit the lateral light from the side surface to the annular image sensor, the endoscope module may sense the image of the object to be detected on the side surface. Furthermore, since the annular stop is disposed on a side of the light incident surface of the annular prism, the endoscope module of the embodiment of the disclosure is more helpful in reducing the distance between the annular prism and the annular lens, further reducing the overall volume of the endoscope module.

In addition, in another embodiment of the disclosure, since the endoscope module includes the first sub-endoscope module and the at least one second sub-endoscope module, the image of the side surface of the object to be detected may be obtained by utilizing the first sub-endoscope module and the second sub-endoscope module at the same time, such that the endoscope module can complete the scanning of the object to be detected within a shorter time, effectively reducing the detection time.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An endoscope module, comprising:
   an annular prism having an annular reflective inclined surface, a light incident surface, and a light emitting surface;
   an annular lens;
   an annular stop, disposed on a side of the light incident surface of the annular prism and surrounding the annular prism;
   an annular image sensor, wherein the annular lens is disposed between the annular prism and the annular image sensor,
   wherein a lateral light from the side of the light incident surface and from outside the endoscope module is reflected to the annular lens by the annular reflective inclined surface after passing through the annular stop and then entering the annular prism, and is then condensed to the annular image sensor by the annular lens; and
   a fixing rod, penetrating centers of the annular prism, the annular lens, and the annular image sensor.

2. The endoscope module according to claim 1, wherein the annular lens and the annular prism are integrally formed.

3. The endoscope module according to claim 1, wherein an inclination angle of the annular reflective inclined surface of the annular prism relative to a central axis of the annular prism falls within a range of 45±3 degrees.

4. The endoscope module according to claim 1, wherein the annular image sensor has a plurality of first pixels, and the first pixels are arranged radially and surround a center of the annular image sensor.

5. The endoscope module according to claim 4, wherein pixel sizes of the first pixels are same as each other.

6. The endoscope module according to claim 4, wherein a quantity of the first pixels within a range from the center of the annular image sensor to a central segmentation line is same as a quantity of the first pixels within a range beyond the central segmentation line in a direction away from the center of the annular image sensor, wherein the central segmentation line is a circular line centered at the center of the annular image sensor, and the range from the center of the annular image sensor to the central segmentation line and the range beyond the central segmentation line in the direction away from the center of the annular image sensor are defined by physical distances on a surface of the annular image sensor.

7. The endoscope module according to claim 1, further comprising:
   a lens, disposed in the fixing rod; and
   an image sensor, disposed in the fixing rod, wherein a frontal light from a side of the annular reflective inclined surface and from outside the endoscope module passes through the lens and is transmitted to the image sensor.

8. The endoscope module according to claim 7, wherein a focal length of the lens is different from a focal length of the annular lens.

9. The endoscope module according to claim 7, wherein the image sensor has a plurality of second pixels, and the second pixels are arranged into an m×n matrix, where m≥2 and n≥2.

10. The endoscope module according to claim 7, further comprising:
    a spinner, connected to the fixing rod; and
    a controller, electrically connected to the spinner and the annular image sensor, wherein the controller controls the spinner to generate a rotational movement of the fixing rod around a central axis of the fixing rod, and the controller overlaps images obtained by the annular image sensor during the rotational movement to increase an effective resolution of the endoscope module.

11. The endoscope module according to claim 10, wherein the rotational movement is a vibration or a restoration after rotation.

12. The endoscope module according to claim 1, further comprising an annular light source, wherein the annular image sensor is disposed between the annular light source and the annular lens.

13. The endoscope module according to claim 12, wherein the annular light source alternately emits light in different colors.

14. The endoscope module according to claim 1, wherein an image of an object to be detected obtained by the annular image sensor is an annular image, and in any radial direction starting from a center of the annular image sensor, an image height of the annular image in the radial direction is proportional to a distance between the object to be detected and the endoscope module in the radial direction.

15. An endoscope module, comprising:
    a first sub-endoscope module, comprising:
    a first annular prism, having a first annular reflective inclined surface, a first light incident surface, and a first light emitting surface;

a first annular lens;

a first annular stop, disposed on a side of the first light incident surface of the first annular prism and surrounding the first annular prism; and a first annular image sensor, wherein the first annular lens is disposed between the first annular prism and the first annular image sensor, wherein a first lateral light from the side of the first light incident surface and from outside the endoscope module is reflected to the first annular lens by the first annular reflective inclined surface after passing through the first annular stop and then entering the first annular prism, and is then condensed to the first annular image sensor by the first annular lens; and at least one second sub-endoscope module, disposed on a side of the first sub-endoscope module, and comprising:

a second annular prism, having a second annular reflective inclined surface, a second light incident surface, and a second light emitting surface;

a second annular lens;

a second annular stop, disposed on a side of the second light incident surface of the second annular prism and surrounding the second annular prism; and a second annular image sensor, wherein the second annular lens is disposed between the second annular prism and the second annular image sensor, wherein a second lateral light from the side of the second light incident surface and from outside the endoscope module is reflected to the second annular lens by the second annular reflective inclined surface after passing through the second annular stop and then entering the second annular prism, and is then condensed to the second annular image sensor by the second annular lens.

\* \* \* \* \*